(12) United States Patent
Finzel et al.

(10) Patent No.: US 6,930,106 B2
(45) Date of Patent: Aug. 16, 2005

(54) INHIBITORS OF HCV NS5B POLYMERASE

(75) Inventors: Barry Craig Finzel, Dexter, MI (US); Lee A. Funk, Chula Vista, CA (US); Robert Charles Kelly, Augusta, MI (US); Matthew T. Reding, University City, MO (US); Nancy Anne Wicnienski, Kalamazoo, MI (US)

(73) Assignee: Pharmacia & UpJohn Company, Kalamazoo, MI (US)

( * ) Notice: Subject to any disclaimer, the term of this patent is extended or adjusted under 35 U.S.C. 154(b) by 53 days.

(21) Appl. No.: 10/610,096

(22) Filed: Jun. 30, 2003

(65) Prior Publication Data

US 2004/0142989 A1 Jul. 22, 2004

Related U.S. Application Data

(60) Provisional application No. 60/392,760, filed on Jul. 1, 2002.

(51) Int. Cl.[7] .................... A61K 31/535; A61K 31/19; A61K 31/165; C07C 321/00; C07C 233/00
(52) U.S. Cl. .................... 514/237.5; 517/570; 517/619; 544/162; 562/431; 562/450; 564/169
(58) Field of Search .............................. 514/237.5, 570, 514/619; 544/162; 562/431, 450; 564/169

(56) References Cited

U.S. PATENT DOCUMENTS

| | | | |
|---|---|---|---|
| 5,552,426 A | 9/1996 | Lunn et al. | |
| 6,177,551 B1 | 1/2001 | Kasina | |
| 6,307,087 B1 | 10/2001 | Buchwald et al. | |
| 6,703,379 B2 * | 3/2004 | Iino et al. | 514/150 |
| 6,777,442 B2 * | 8/2004 | Haning et al. | 514/532 |

FOREIGN PATENT DOCUMENTS

| | | |
|---|---|---|
| WO | WO 98/33501 | 8/1998 |
| WO | WO 00/06529 | 2/2000 |
| WO | WO 00/10573 | 3/2000 |
| WO | WO 01/77091 | 10/2001 |
| WO | WO 02/04425 | 1/2002 |

OTHER PUBLICATIONS

Amatore, C., "Role of dba in the Reactivity of Palladium (0) Complexes Generated in Situ from Mixtures of Pd(dba)$_2$ and Phosphines," *Coordination Chemistry Reviews*, 1998, 511–528, vol. 178–180.

Baudoin, O., "Cyclobisintercaland Macrocycles: Synthesis and Physiochemical Properties of Macrocyclic Polyamines Containing Two Crescent–Shaped Dibenzophenanthroline Subunits," *Journal of Organic Chemistry*, 1997, 5458–5470, vol. 62.

Behrens, et al., "Identification and Properties of the RNA–dependent RNA Polymerase of Hepatitis C. Virus," *EMBO J*, 1996, 12–22, vol. 15, No. 1.

Berg, et al., Pharmaceutical Salts, *Journal of Pharmaceutical Sciences*, 1977, 1–19, vol. 66, No. 1.

Black, D. S., *Aust. Journal Chem.*, 1983, 2395–2406, vol. 36, No. 12.

Bourson, J., "Synthèse et Oxydo–rèduction des Sels de Diphènyl–1,3 Benzimidazolium," J., *Bull. Soc. Chim, Fr.*, 1970, 1867–1872, No. 5.

Buchwald, et al., "An Improved Catalyst System for Aromatic Carbon Nitrogen Bond Formation: The Possible Inveolvement of Bis(Phosphine) Palladium complexes as Key Intermediates," *J. Amer. Chem. Soc.*, 1996, 7215–7216, vol. 118.

Buchwald, et al., "A Highly Active Catalyst for the Room–Temperature Amination and Suzuki Coupling of Aryl Chlorides," *Angew. Chem. Int. Ed.*, 1999, 2413–2416, vol. 38, No. 16.

Buchwald, et al., "Scope and Limitations of the Pd/BINAP–Catalyzed Amination of Aryl Bromides," *Journal of Organic Chemistry*, 2000, 1144–1157, vol. 65.

Buchwald, et al., "Palladium–catalyzed Amination of Aryl Halides and Sulfonates," *Journal of Organometallic Chemistry*, 1999, 125–146.

Ebisawa, et al., "Retinoid X Receptor–Antagonistic Dizzepinylbenzoic Acids," *Chem. Pharm Bull.*, 1999, 1778–1786, vol. 47, No. 12.

Ferrari, et al., "Characterization of Soluble Hepatitis C Virus RNA–Dependent RNA Polymerase Expressed in *Escherichia coli*," *Journal of Virology*, 1999, 1649–1654, vol. 73, No. 2.

Hartwig, et al., A Second–Generation Catalyst for Aryl Hailide Amination: Mixed Secondary Amlines from Aryl Halides and Primary Amines Catalyzed by (DPPF) PdCl$_2$, *J. Amer. Chem Soc.*, 1996, 7217–7218, vol. 118.

Hartwig, et al., "Discrete High Molecular Weight Triarylamine Dendrimers Prepared by Palladium–Catalyzed Amination," *J. Amer. Chem Soc.*, 1997, 11695–11696, vol. 119.

(Continued)

*Primary Examiner*—Deborah C. Lambkin
(74) *Attorney, Agent, or Firm*—Jeffrey H. Tidwell; Bryan C. Zielinski; Peter C. Richardson

(57) ABSTRACT

The present invention provides compounds of Formula I, compositions and methods that are useful for treating viral infections and associated diseases, particularly HCV infections and associated diseases.

Formula I

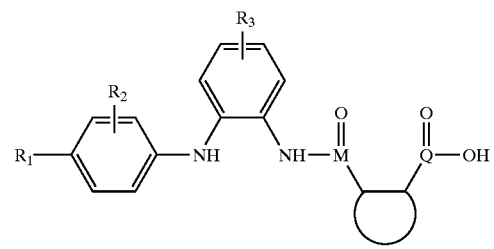

12 Claims, No Drawings

OTHER PUBLICATIONS

Hartwig, et al.,"Palladiium–Catalyzed C–Nsp$^2$) Bond Formation: N–Arylation of Aromoatic and Unsaturated Nitrogen and the Reductive Elimination Chemistry of Palladium Azolyl and Methyleneamido Complexes," *J. Amer. Chem Soc.*, 1998, 827–828, vol. 120.

Houghton, M., *Hepatitis C Viruses Fields Virology*, 1996, 1035–1058, Third Edition, Edited by B. N. Fields, Kippincott–Raven Publishers, Philadelphia, PA.

Ishido, et al., "Complex Formation of NS5B and NS4A Proteins of Hepatitis C Virus," *Biochemical and Biophysical Research Communications*, 1998, 35–40, vol. 244.

Kato, et al., "Molecular Cloning of the Human Hepatitis C Virus Genome from Japanese Patients with Non–A, Non–B Hepatitis," *Proc. Natl. Acad. Sci. USA*, 1990, 9524–9528, vol. 87.

Lau, et al., "Application of Six Hepatitis C Virus Genotyping Systems to Sera from Chronic Hepatitis C Patients in the United States," *The Journal of Infectious Diseases*, 1995, 281–289, vol. 171, No. 2.

Lohmann, et al., "/Biochemical Properties of Hepatitis C Virus NS5B RNA–Dependent RNA Polymerase and Identification of Amino Acid Sequence Motifs Essential for Enzymatic Activity," *Journal of Virology*, 1997, 8416–8428, vol. 71, No. 11.

March, et al., *Advanced Organic Chemistry: Reactions, Mechanisms, and Structure*, 2001, 5$^{th}$ Edition, Wiley–Interscience.

Nagar, et al., *Proc. Natl. Acad. Sci. India, Section A*, 1993, 617–622, vol. 63, No. 4.

Umemiya, et al., "Regulation of Retinoidal Actions by Diazepinylbenzoic Acids.[1] Retinoid Synergists Which Activate the RXR–RAR Heterodimers," *Journal of Medicinal Chemistry*, 1997, 4222–4234, vol. 40.

Van Doorn, L. J., "Review: Molecular Biology of the Hepatitis C Virus," *Journal of Medical Virology*, 1994, 345–356, vol. 43.

Webster, et al., "HCV Genotypes–Role in Pathogenesis of Disease and Response to Therapy," *Balliere's Clinical Gastroenterology*, 2000, 229–240, vol. 14, No. 2.

Wuts & Greene, *Protective Groups in Organic Synthesis*, Wiley–Interscience, New York, USA.

* cited by examiner

INHIBITORS OF HCV NS5B POLYMERASE

CROSS REFERENCE

This application claims the benefit of the following provisional application: U.S. Ser. No. 60/392,760, filed Jul. 1, 2002, under 35 USC 119(e)(i), which is incorporated herein by reference in its entirety.

FIELD OF THE INVENTION

The present invention relates to compounds, process for their synthesis, compositions and methods for the treatment and prevention of hepatitis C virus (HCV) infection. In particular, the present invention provides novel compounds, pharmaceutical compositions containing such compounds and methods for using these compounds in the treatment or prevention of HCV infection. The present invention also provides processes and intermediates for the synthesis of these compounds.

BACKGROUND OF THE INVENTION

Hepatitis C virus (HCV) is the major etiological agent of post-transfusion and community-acquired non-A non-B hepatitis worldwide. It is estimated that over 150 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death. The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy.

Therefore, a need exists for the development of effective antiviral agents for treatment of HCV infection that overcomes the limitations of existing pharmaceutical therapies.

General Viral polymerases are attractive targets for antiviral drug development. For example, inhibitors of Viral RNA polymerase activity have been described; see, for example, JAEN, Juan, et. al., WO 0177091, Altamura et. al., WO 00/06529 and Bailey et. al., WO 00/10573, which references are incorporated by reference herein.

The HCV protein NS5B is an RNA dependent RNA polymerase, see, e.g., Lohmann et al. (1997) J Virol. 71:8416–8428, Behrens et al. (1996) EMBO J 15:12–22 and Ishido et al. (1998) Biochem. Biophys. Res. Comm. 244:35–40, which references are incorporated by reference herein. The sequence of various genotypes of HCV NS5B are known (Kato et al. (1990) Proc. Natl. Acad. Sci. USA. 87:9524–9528; Webster, G., et al. (2000) Balliere's Clinical Gastroenterology 14, 229–240; van Doorn, L. J. (1994) J. of Medical Virology 43, 345–356; Houghton, M. (1996) Hepatitis C viruses Fields Virology: Third Edition, edited by B. N. Fields, D. M. Knipe, P. M. Howley, et al. Lippincott-Raven Publishers, Philadelphia, pp. 1035–1058; Lau, J. Y. et.al., J Infect Dis. 1995, 171(2), 281–9). However, NS5B contains sequence motifs that are highly conserved among all the RNA-dependent RNA polymerases characterized to date.

SUMMARY OF THE INVENTION

The present invention provides compounds, compositions and methods that are useful for treating viral infections and associated diseases, particularly HCV infections and associated diseases. The compounds of the invention inhibit viral replication, preferably HCV replication. The methods of the invention comprise administering to an infected or susceptible host a therapeutically or prophylactically effective amount of a compound as represented by Formula 1, Formula I

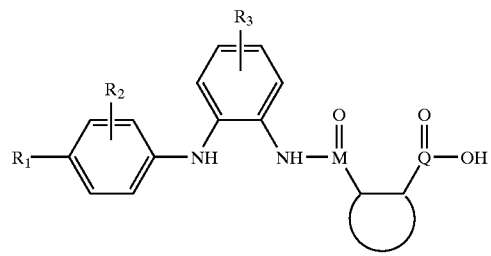

wherein

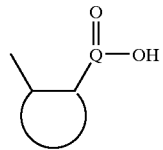

represents a five or six membered saturated, partially unsaturated or aromatic ring optionally containing 1 or 2 heteroatoms of O, N or S, or a pharmaceutically acceptable salt or prodrug thereof.

DETAILED DESCRIPTION OF THE INVENTION

Abbreviations and Definitions

The abbreviations used herein are conventional, unless otherwise defined.

The terms "treat", "treating" and "treatment" refer to a method of alleviating or abrogating a disease and/or its attendant symptoms.

The terms "prevent", "preventing" and "prevention" refer to a method of barring a subject from acquiring a disease. As used herein, "prevent", "preventing" and "prevention" also include reducing a subject's risk of acquiring a disease.

The term "therapeutically effective amount" refers to that amount of the compound being administered sufficient to prevent development of or alleviate to some extent one or more of the symptoms of the disease being treated.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

"Flaviviridae virus", as used herein, refers to a virus of the family Flaviviridae, which family includes the Flavivirus, Pestivirus and Hepacivirus or hepatitis C-like virus genera. Representative species of the genus Flavivirus include yellow fever virus, tick-borne encephalitis virus, Rio Bravo virus, Japanese encephalitis virus, Tyuleniy virus, Ntaya virus, Uganda S virus, Dengue virus and Modoc virus. Representative species of the genus Pestivirus include bovine diarrhea virus, border disease virus and hog cholera virus. A representative species of the genus of hepatitis C-like viruses is hepatitis C virus. Unassigned viruses in the family Flaviviridae are included in the meaning of Flaviviridae virus.

The term "modulate" refers to the ability of a compound to increase or decrease the catalytic activity of a viral polymerase, e.g. a viral RNA polymerase. A modulator preferably activates the catalytic activity of a viral polymerase or more preferably activates or inhibits the catalytic activity of a viral polymerase depending on the concentration of the compound exposed to the viral polymerase or most preferably inhibits the catalytic activity of a viral polymerase.

The term "modify" refers to the act of altering, in whole or in part, the structure of a molecule, e.g., a protein. Modification may be covalent or noncovalent, and includes, but is not limited to, aggregation, association, substitution, conjugation and/or elimination of a chemical group. Modification may alter the function or other properties (e.g., chemical, physical) of the molecule.

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e. $C_1$–$C_8$ means 1–8 eight carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. A "lower alkyl" is a shorter chain alkyl having eight or fewer carbon atoms.

The terms "alkoxy . . . alkylcylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NRR' wherein the R groups can be the same or different alkyl groups.

The term "heteroalkyl," by itself or in combination with another term, means, unless otherwise stated, a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$. Also included in the term "heteroalkyl" are those radicals described in more detail below as "heterocycloalkyl".

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopropyl, cyclobutyl, cyclopentyl, cyclohexyl, 1-cyclohexenyl, 3-cyclohexenyl, cycloheptyl, and the like. Examples of heterocycloalkyl include 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "Fluoroalkyl," are meant to include monofluoroalkyl and polyfluoroalkyl.

The term "aryl," employed alone or in combination with other terms (e.g., aryloxy, arylthioxy, aralkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 1-indolyl, 5-indolyl, 1-isoquinolyl, 5-isoquinolyl, 2-quinoxalinyl, 5-quinoxalinyl, 3-quinolyl, and 6-quinolyl.

Substituents for each of the above noted aryl ring systems are selected from the group of acceptable substituents described below. The term "aralkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy) propyl, and the like). Each of the above terms (e.g., "alkyl . . . heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R"—SR', -halogen, —SiR'R"R, —OC(O) R', —C(O)R', —CO$_2$R', CONR'R", —OC(O)NR'R"—NR'C (O)R', —NR'—C(O)NR"R'", —NR'COOR", —NH—C (NH$_2$)=NH, —NR'C(NH$_2$)=N—H, —NH—C(NH$_2$) =NR', —S(O)R', S(O)$_2$R', —S(O)$_2$NR'R", —CN and —NO$_2$ in a number ranging from zero to (2N+1), where N is the total number of carbon atoms in such radical. R', R" and X" each independently refer to hydrogen, unsubstituted C1-C0alkyl and heteroalkyl, unsubstituted aryl, aryl substituted with 1–3 halogens, unsubstituted alkyl, alkoxy or thioalkoxy groups, or aryl-(C1–C4)alkyl groups. When R' and R" are attached to the same nitrogen atom, they can be combined with the nitrogen atom to form a 3–7 membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: halogen, —OR, —OC(O)R, —NR'R", —SR, —R', —CN, —NO$_2$, —CO$_2$R', —CONR'R:', —C(O) R', —OC(O)NR'R", —NR"C(O)R', —NR"C(O)$_2$R', —NR'—C(O)NR"R'", —NH—C(NH$_2$)=NH, —NR'C (NH$_2$)=NH, —NH—C(NH$_2$)=NR', —S(O)R', —S(O)$_2$R', —S(O)$_2$NR'R", —N$_3$, —CH(Ph)$_2$, perfluoro(CI–C4)alkoxy, and perfluoro(CI–C4)alkyl, in a number ranging from zero to the total number of open valences on the aromatic ring system; and where R', R" and R'" are independently selected from hydrogen, (C1–C8)alkyl and heteroalkyl, unsubstituted aryl, (unsubstituted aryl)-(C1–C4)alkyl, and (unsubstituted aryloxy-(C$_1$–C$_4$)alkyl.

Two of the substituents on adjacent atoms of the aryl ring may optionally be replaced with a substituent of the formula —S—C(O)—(CH$_2$)q—R—, wherein S and R are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)$_w$—B—, wherein A and B are independently —CH$_2$—, —O—, —NH—, —S—, —S(O)—, —S(O)$_2$—, —S(O)$_2$NR'— or a single bond, and w is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_w$-G-(CH$_2$)$_{w'}$—, where w and w' are independently integers of from 0 to 3, and G is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1–C6)alkyl.

As used herein, the term "heteroatom" is meant to include oxygen (O), nitrogen (N),) and sulfur(S).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactouronic acids and the like (see, for example, Berge, S. M., et. al. (1977) J. Pharm. Sci., 66:1–19). Certain specific compounds of the present invention contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention unless otherwise stated.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Description of the Embodiments

Viral RNA polymerase is required for the transcription of genomic RNA, which process is required for replication of the genome of an RNA virus. Therefore, inhibition of viral RNA polymerase will inhibit viral replication. The present invention

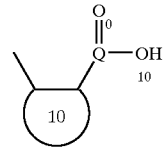

provides compounds having antiviral activity. The compounds of the invention block viral replication by specifically inhibiting the activity of a viral polymerase.

In a first group of embodiments, the compounds useful for modification of a viral RNA-dependent RNA polymerase protein are of Formula I

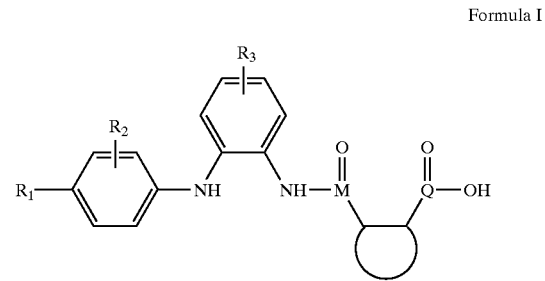

Formula I wherein represents a five or six membered saturated, partially unsaturated or aromatic ring optionally containing 1 or 2 heteroatoms of O, N or S;

$R_2$ and $R_3$ represent 1 to three substituents independently selected from the group consisting of halogen, —CN, N(R)(R'), —NO$_2$, fluoroalkyl, fluroalkyloxy, alkyl, aryl, aralkyl, arlyoxy, aralkyloxy, alkylthio, arylthio, and heteroalkyl;

R, R' and R" are independently H or $C_1$–$C_6$ alkyl;

R and R' may be taken together to form a 3 to 7 membered ring optionally containing an additional heteroatom of —O—, —NR"—, —S— or —SO$_n$—;

$R_1$ is selected from the group consisting of H, —CN, and —(CH$_2$)$_n$—N(R$_5$)R$_6$;

$R_5$ is H or $C_1$–$C_6$ alkyl;

$R_6$ is selected from the group consisting of H, $C_1$–$C_6$ alkyl, aryl, substituted aryl, aralkyl, heteroaryl, heteroaralkyl, heteroalkyl and substituted heteroalkyl;

$R_5$ and $R_6$ may be joined together to form a 5 to 7 membered ring optionally containing an additional heteroatom of —NR—, —O—, —S— or —SO$_n$—;

M and Q are independently —C— or —S(=O)—;

Each n is independently 0, 1 or 2.

Non-limiting examples of the invention are shown in Table 1.

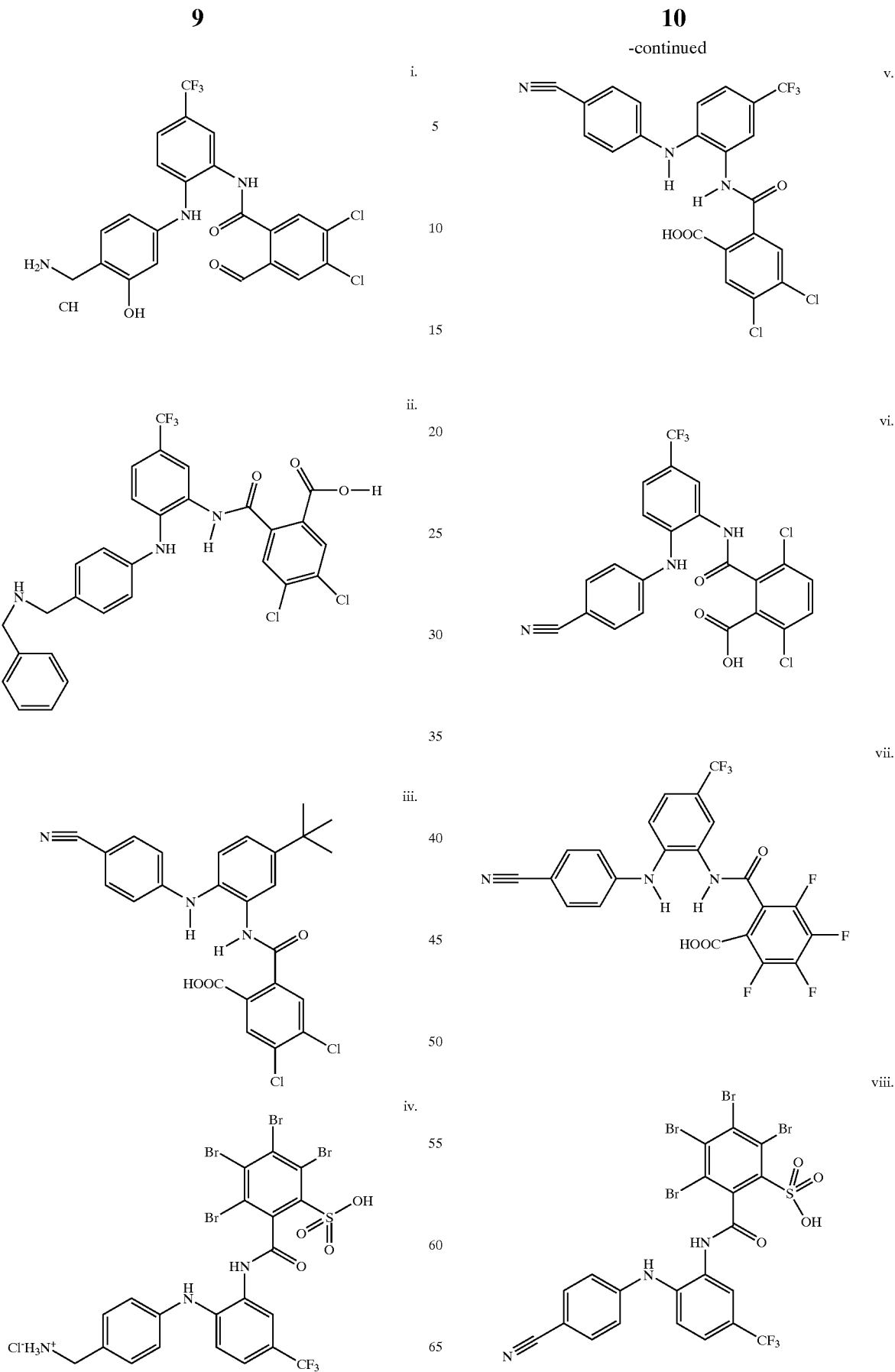

ix.
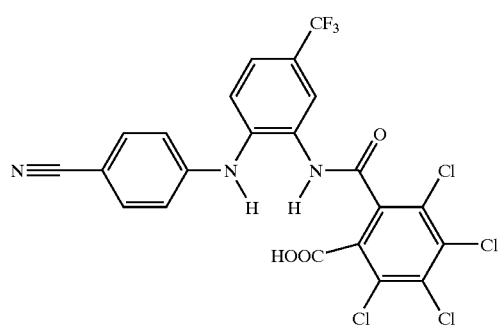
x.
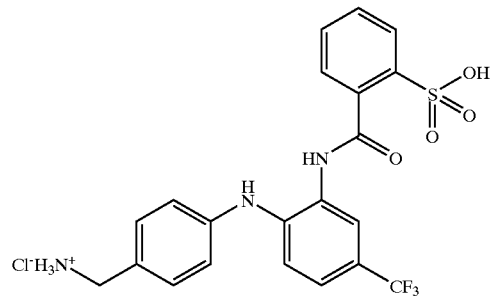
xi.
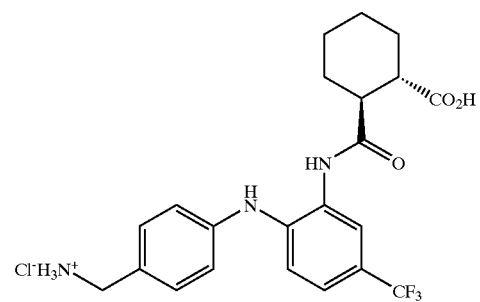
xii.
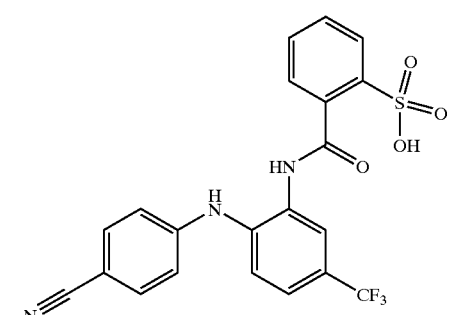
xiii.
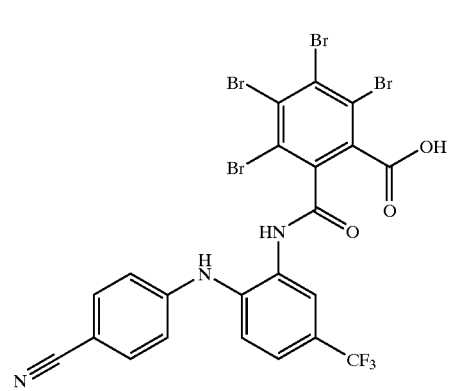
xiv.
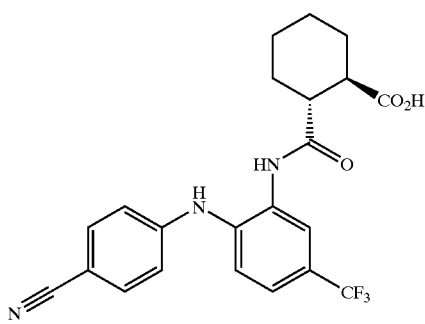
xv.
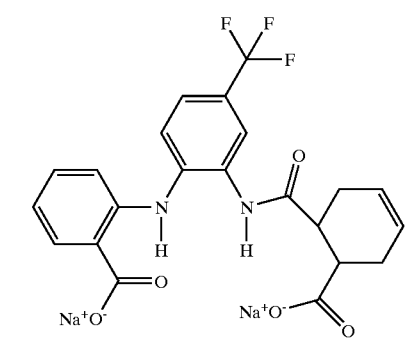
xvi.
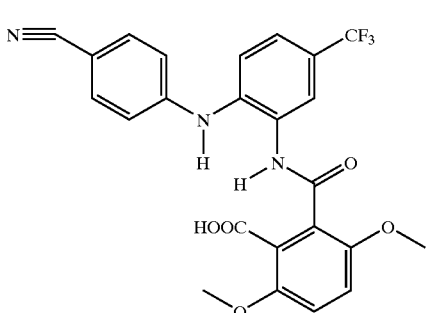
xvii.
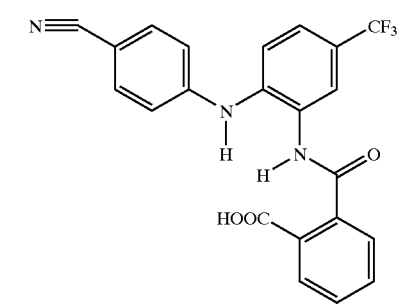
xviii.
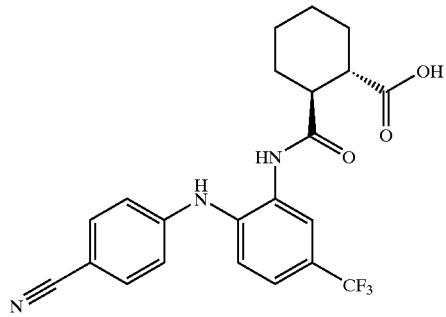

-continued
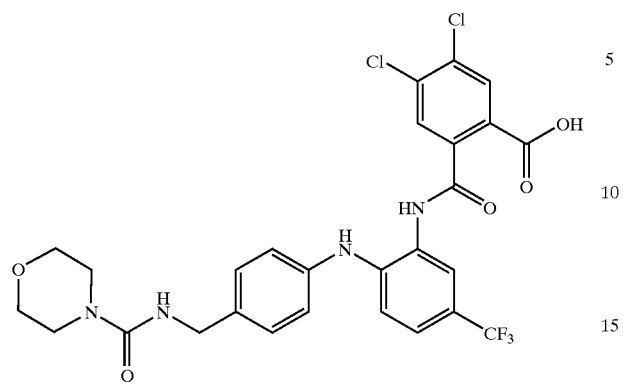
xix.
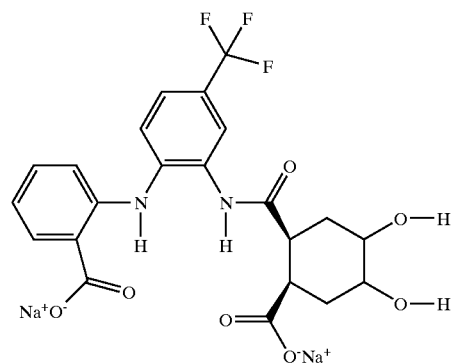
xx.
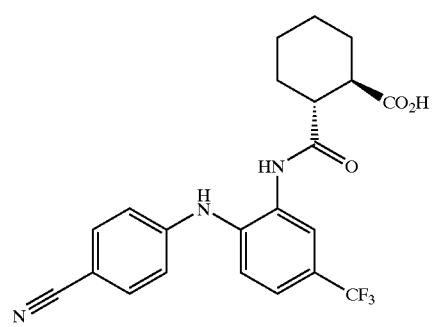
xxi.
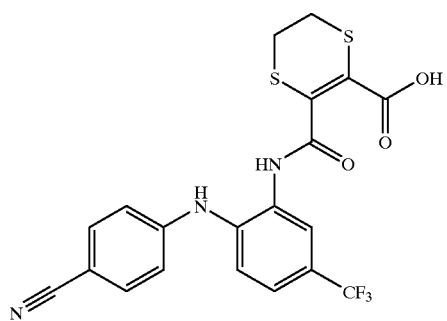
xxii.
-continued
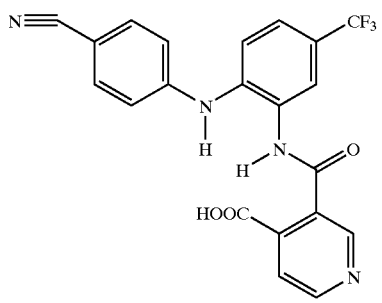
xxiii.
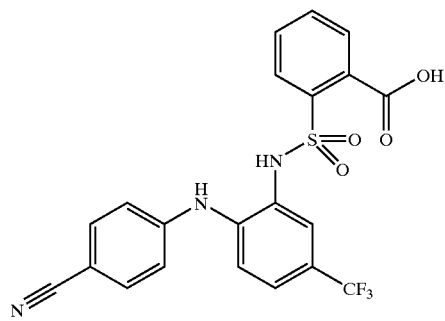
xiv.
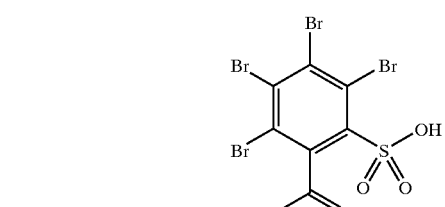
xxv.
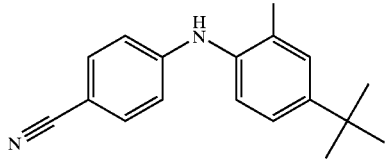
xxvi.
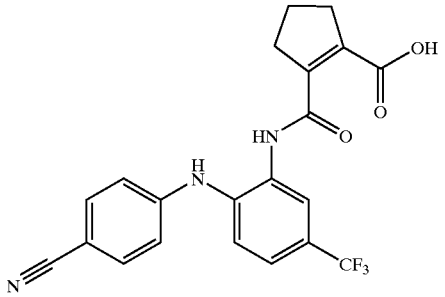
xxvii.
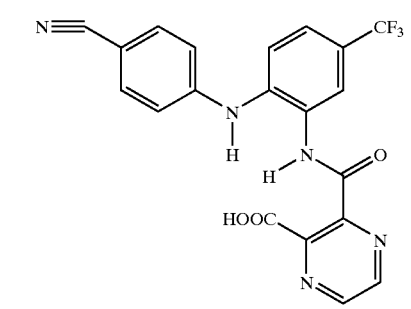

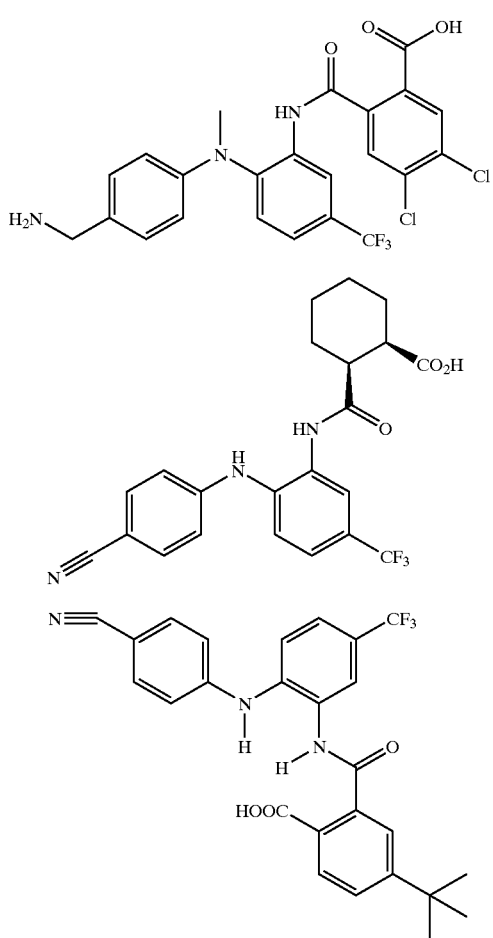

Analysis of the Compounds

The subject compounds and compositions may be demonstrated to have pharmacological activity, e.g., antiviral activity, in in vitro and in vivo assays, as known in the art. See for example Behrens, S. E., et.al EMBO J. 15:12–22; Lohmann, V., et.al., 1997, J. Virol. 71:8416–8428; Ferrari, E., et al., 1999. J. Virol. 73:1649–1654; Bealieu, P. L. et.al., WO0204425 A2; Perni, R. B. et. al., WO9833501; which references are incorporated by reference herein.

The subject compounds and compositions are capable of specifically inhibiting or suppressing a viral infection, e.g., an HCV infection. An in vivo assessment of the antiviral activity of the compounds of the invention may be made using an animal model of viral infection, e.g., a primate model. Cell-based assays may be performed using, for example, a cell line directly infected with a virus. Cell-based assays for activity against a specific viral component, for example, a polymerase, may also be performed. Additionally, biochemical or mechanism-based assays, for example, transcription assays using a purified protein, Northern blot, RT-PCR, etc., may be performed.

The above-described assays are exemplary and not intended to limit the scope of the invention. The skilled practitioner can appreciate that modifications can be made to conventional assays to develop equivalent assays that obtain the same result.

High throughput assays for the presence, absence, quantification, or other properties of particular compounds are well known to those of skill in the art. Such assays may be adapted to identify compounds capable of modifying a viral RNA dependent RNA polymerase protein, e.g., NS5B using functional protein. Preferred assays thus detect enhancement or inhibition of HCV RNA-dependent RNA activity.

Compositions

In view of the antiviral activity associated with the compounds described above, the present invention further provides pharmaceutical compositions comprising one or more of the above compounds in combination with a pharmaceutically acceptable excipient.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a prodrug, which can be metabolically or chemically converted to the subject compound by the recipient host. A wide variety of prodrug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Methods of Use

In yet another aspect, the present invention provides novel methods for the use of the foregoing compounds and compositions. In particular, the invention provides novel methods for treating or preventing viral infections, e.g., HCV infection. The invention also provides novel methods for treating or preventing diseases resulting from, in whole or in part, viral infections, preferably diseases resulting from, in whole or in part, infection, such as hepatitis C, cirrhosis, chronic liver disease and hepatocellular carcinoma. The methods typically involve administering to a patient an effective amount of one or more of the subject compounds or compositions.

The compositions may be advantageously combined and/or used in combination with other antiviral agents which are either therapeutic or prophylactic agents, and different from the subject compounds. The compositions may also be advantageously combined and/or used in combination with agents that treat conditions often associated with the viral infections that are sensitive to the present compounds, such as anti-HIV agents or immunosuppressive agents. In many instances, administration in conjunction with the subject compositions enhances the efficacy of such agents. Accordingly, the present compounds, when combined or administered in combination with other antiviral agents, can be used in dosages which are less than the expected amounts when used alone, or less than the calculated amounts for combination therapy.

Exemplary treatment options for hepatitis C (HCV) include interferons, e.g., interferon alfa-2b, interferon alfa-2a, and interferon alfacon-1. Less frequent interferon dosing can be achieved using pegylated interferon (interferon attached to a polyethylene glycol moiety which significantly improves its pharmacokinetic profile). Combination therapy with interferon alfa-2b (pegylated and unpegylated) and ribavarin has also been shown to be efficacious for some patient populations. Other agents currently being developed include RNA replication inhibitors, antisense agents, therapeutic vaccines, protease inhibitors, helicase inhibitors and antibody therapy (monoclonal and polyclonal).

The compounds and compositions of the present invention may also be used with agents that enhance the body's immune system, including low-dose cyclophosphamide, thymostimulin, vitamins and nutritional supplements (e. g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric 5 presentation of antigen and an adjuvant.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

Preparation of the Compounds

Some of compounds of this invention are commercially available. For example, 4-amino-N-[5-amino-2-(phenylamino)phenyl]-benzamide, is available from Ambinter, 46 quai Louis, Bleriot, Paris, F-75016, France and N-[2-(phenylamino)phenyl]-benzamide is available from Scientific Exchange, Inc., Pine River Road, P O Box 918, Center Ossipee, N.H., 03814, USA. The compounds of this invention can also be prepared by methods described in the chemical literature. For example, methods for the preparation of the compounds are described by Ebisawa, E. et.al., *Chem. Pharm. Bull.* 47, 1778 (1999), H. Umemiya et.al., *J. Med. Chem.,* (1997) 40, 4222 and Lunn, W. H. W., et.al., U.S. Pat. No. 5,552,426.

To the advantage of the practitioner, the compounds of this invention can also be prepared by one or more of the following schemes described below. The preparation of the various diaryl amine products and intermediates of this invention is based on variations of the palladium catalysed amine coupling reaction methodology described in the literature (See for example Buchwald, S. L., et.al., U.S. Pat. No. 6,307,087; Buchwald, S. L. et.al., *J. Org. Chem.* (2000) 65, 1144; Buchwald, S. L. et. al., *J. Organomet. Chem.* (1988) 348, 95; Amatore, C., *Coord. Chem. Rev.,* (1998) 178–80, 511; Buchwald, S. L., et.al., *Angew. Chem. Int. Ed.,* (1999) 38, 2413; Buchwald, S. L., et.al., *J. Amer. Chem. Soc.,* (1996) 118, 7215; Hartwig, J. F., et.al., *J. Amer. Chem. Soc.,* (1996) 118, 7217; Hartwig, J. F., et.al., *J. Amer. Chem. Soc.,* (1997) 119, 11695; Hartwig, J. F., et.al., *J. Amer. Chem. Soc.,* (1998) 118, 827). In general, the methodolgy provides the diaryl amine products and intermediates of the invention under mild reaction conditions tolerant of a wide variety of substituents. Other modifications and preparations are known in the art: March, et.al., March's Advanced Organic Chemistry: Reactions, Mechanisms, and Structure, 5th Edition, Wiley-Interscience, 2001; Wuts and Greene, Protective Groups in Organic Synthesis, Wiley-Interscience.

Scheme 1:

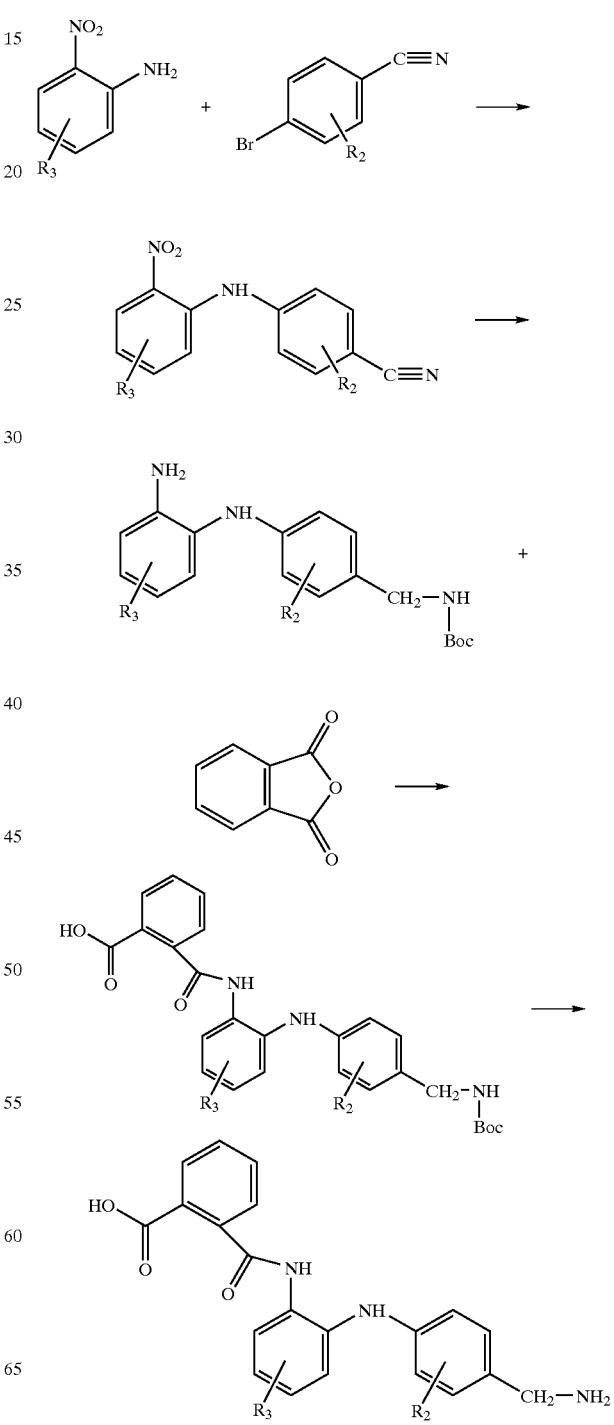

Scheme 2:
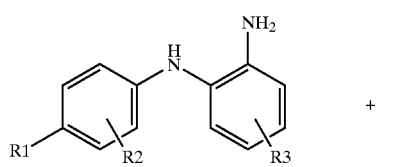
+
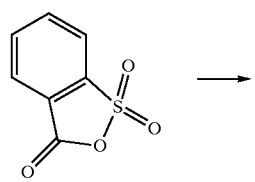
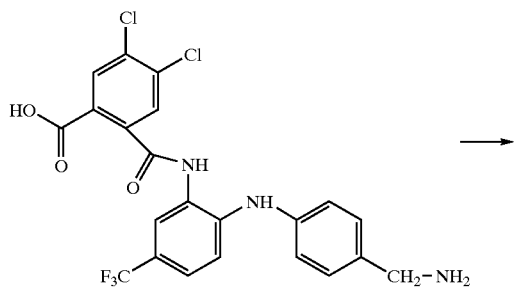
Scheme 3:
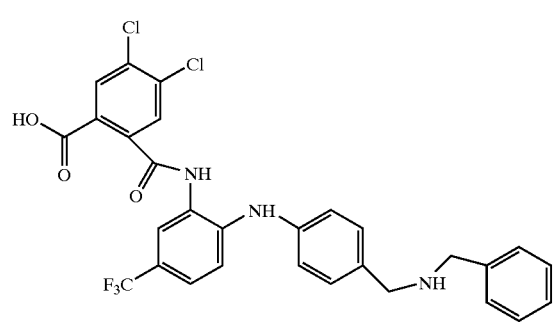
Scheme 4:
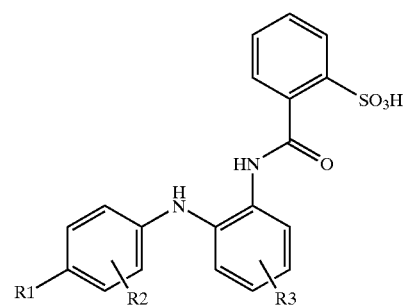
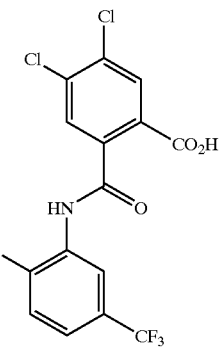
Scheme 5:
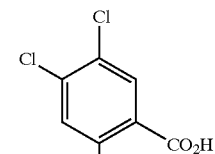
+
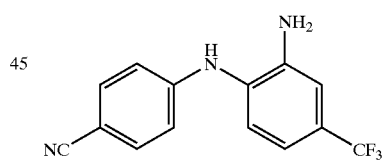
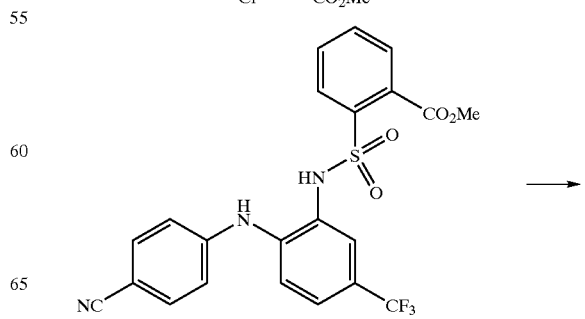

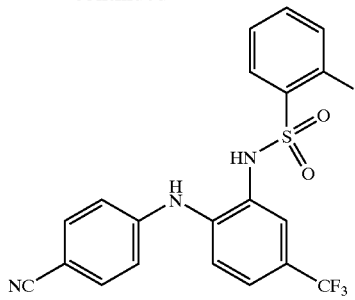

cyanide, palladium (II) iodide, palladium (II) nitrate hydrate, palladium (II) oxide, palladium (II) sulfate dihydrate, palladium (II) trifluoroacetate, tetraamine palladium (II) tetrachloropalladate (II), tetrakis(acetonitrile)palladium (II) tetrafluoroborate, tetrakis(triphenylphosphine)palladium (0) and the like.

Suitable ligands include tri-o-tolylphosphine, 2,2'-Bis(diphenylphosphino)-1,1'-binaphthyl (BINAP), 1,1'-bis(diphenylphosphino)ferrocene, 2-(di-t-butylphosphino)biphenyl, tri-2-furylphosphine, tris(2,4-di-t-butylphenyl)phosphite, dicyclohexyl 2-(2'-N,N-dimethylamino)biphenylphosphine, 1-[(1S)-1-(dimethylamino)ethyl]-2-(diphenylphosphino)-Ferrocene (PPFA), bis[2-(diphenylphosphino)phenyl] ether (DPEphos) and the like.

Scheme 6:

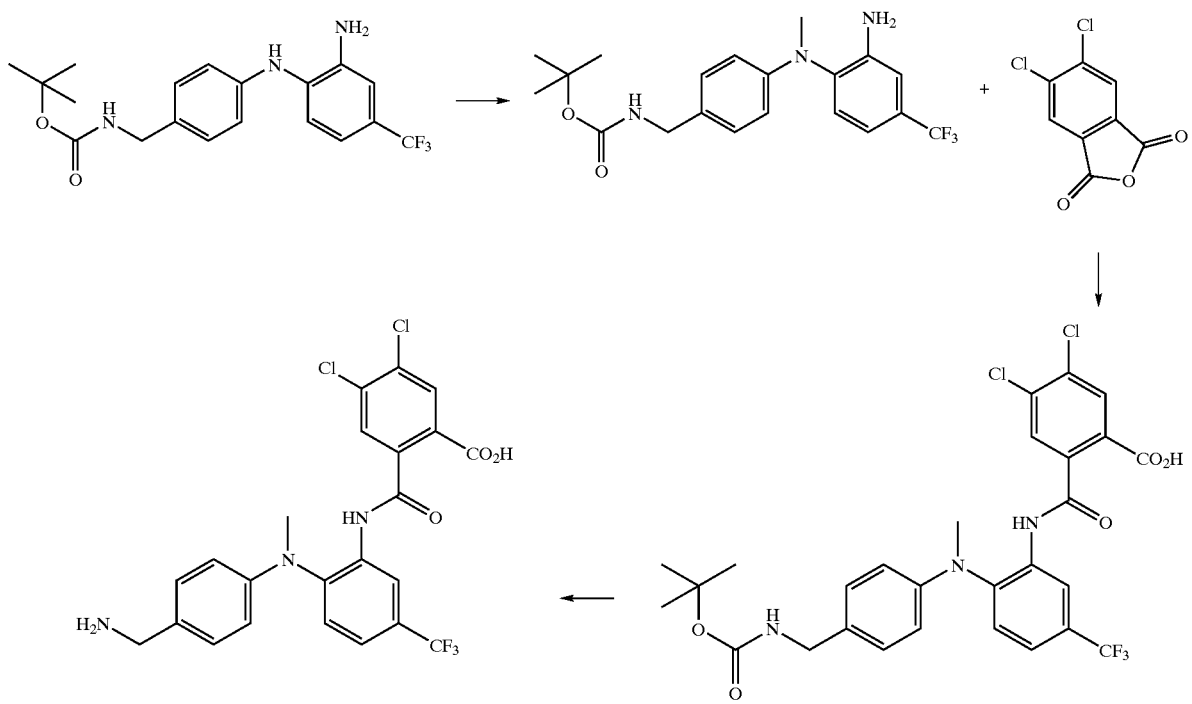

In Scheme I R groups are as defined above. M is chosen from the group Cl, Br, I or $OSO_2CF_3$. Suitable sources of palladium include tris(dibenzylideneacetone)dipalladium (O) ($Pd_2dba_3$), palladium acetate bis[μ-(acetato-κO: κO')]bis[[2-[bis(2-methylphenyl)phosphino-κP]phenyl]methyl-κC]di-palladium, bis[1,2-bis(diphenylphosphino)ethane] palladium (0), bis(2-methylallyl)palladium chloride dimer, bis(tri-t-butylphosphine)palladium (0), bis(tricyclohexylphosphine)palladium (0), chloro(di-2-norbornylphosphino)(2'-imethylamino-1,1'-biphenyl-2-yl) palladium (II), diacetatobis(triphenylphosphine)palladium (II), dichlorobis(acetonitrile)palladium (II), dichlorobis(benzonitrile)palladium (II), dichloro(1,2-bis(diphenylphosphino)ethane)palladium (II), dichloro[1,1'-bis(diphenylphosphino)ferrocene]palladium (II) dichloromethane adduct, trans-dichlorobis(tricyclohexylphosphine)palladium (II), trans-dichlorobis(triphenylphosphine)palladium (II), trans-dichlorobis(tri-o-tolylphosphine)palladium (II), dichloro(1,5-cyclooctadiene)palladium (II), trans-dichlorodiammine palladium (II), palladium (II) acetate, palladium (II) acetylacetonate, palladium (II) bromide, palladium (II) chloride, palladium (II)

Bases suitable for the reactions include $Cs_2CO_3$, lithium di-o-tolylamide, sodium t-butoxide, potassium t-butoxide, lithium bis-trimethylsilylamide, lithium diisopropylamide, potassium phosphate, sodium 2,4,6-tri-t-butylphenoxide, sodium carbonate, lithium carbonate, potassium carbonate, rubidium carbonate, triethylamine, diazabicycloundecane, Hunig's base, pyridine, and the like.

Suitable solvents include toluene, xylene, acetonitrile, dimethoxyethane, tetrahydrofuran, dioxane, dimethylformamide and the like.

It is obvious to one of ordinary skill in the art that further variations and transformations of the products and intermediates of Schemes 1–4 are readily achieved using methods common in the art. These transformations include for example, ester, nitrile and amide hydrolysis; ester, amide and nitrile reduction; primary and secondary amine alkylation, acylation, aroylation; alcohol acylation, aroylation and alkylation and the like.

EXAMPLES

The following examples further illustrate the preparation and analysis of compounds of the invention. The examples are illustrative only and not intended to limit the scope of the invention in any way. Reagents and solvents can be obtained from commercial sources such as Aldrich Chemical Co. (Milwaukee, Wis., USA). All commercially obtained reagents are used as received without further purification. Solvents are used as received or dried over appropriate drying agents and distilled. Proton NMR experiments are carried out on a Bruker 400 MHz spectrometer, and chemical shifts are reported in ppm downfield from internal TMS. Carbon NMR experiments are carried out on a Bruker 500 MHz spectrometer, and chemical shifts are reported in ppm relative to the central line of deuteriochloroform at 77.0 ppm. Low resolution mass spectra (ESI) are obtained on a Micromass Platform C spectrograph. Low resolution mass spectra (EI) and high resolution mass spectra (FAB), as well as IR spectra and elemental analyses are conducted by the Pharmacia analytical laboratory. Flash column chromatography is carried out on Biotage 40 prepacked columns, while preparative TLC is carried out on Merck silica gel $F_{254}$-coated plates with 0.25 mm or 0.5 mm silica layers. Unless otherwise noted, reactions are carried out in dry glassware under a nitrogen atmosphere.

Example 1 According to Scheme 1

2-({[2-{[4-(aminomethyl)phenyl]amino}-5-(trifluoromethyl)phenyl]amino}carbonyl)-4,5-dichlorobenzoic acid hydrochloride (i)

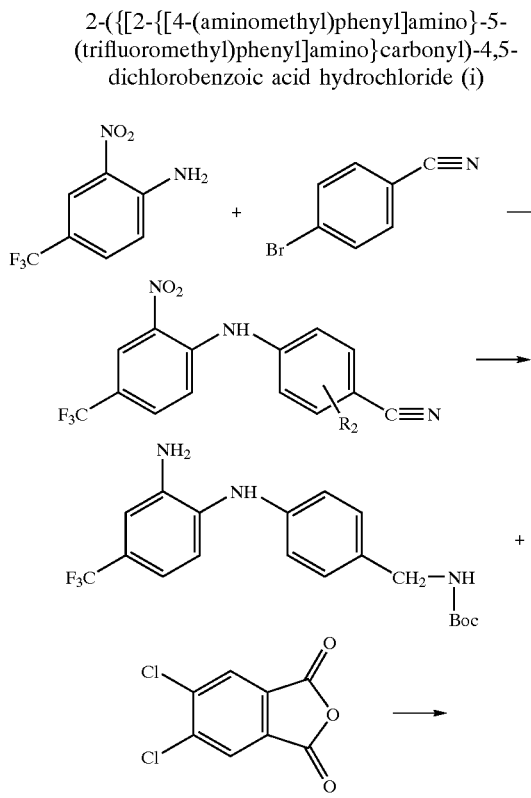

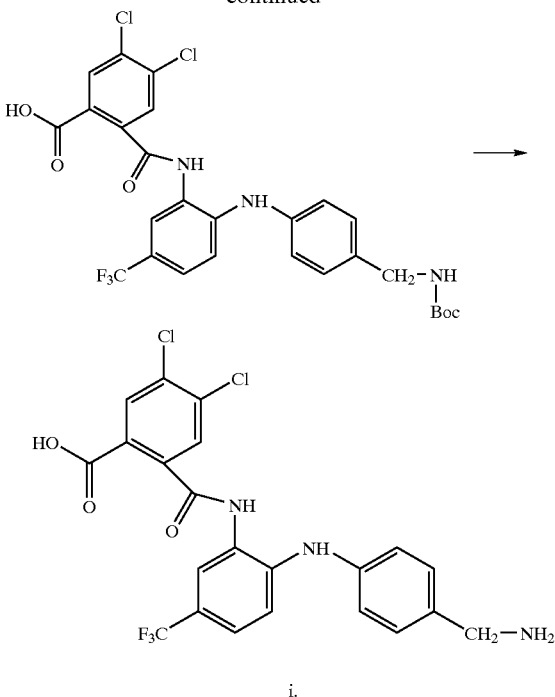

i.

4-bromobenzonitrile (218 mg, 1.2 mmol), 2-nitro-4-(trifluoromethyl)aniline (206 mg, 1.0 mmol), $Pd_2dba_3$ (23 mg, 0.025 mmol), $PCy_2dmab$ (30 mg, 0.075 mmol), and $Cs_2CO_3$ (489 mg) are added to a round bottom flask. The flask is evacuated and filled with nitrogen two times and then left under vacuum for 5 min. After filling with nitrogen, toluene (4 mL Sureseal, degassed with nitrogen for 20 min) is added via syringe and the resultant dark red/black solution is heated to 100° C. with an oil bath. After 18 hr, the solution is cooled to room temperature and excess ethyl acetate is added. After washing with 1M HCl two times, the organic layer is washed with brine, dried over $MgSO_4$, filtered through Celite, and concentrated to give crude material. This solid was purified by flash chromatography to afford 4-{[2-nitro-4-(trifluoromethyl)phenyl]amino}benzonitrile. The yield is 288 mg (94%).

4-{[2-nitro-4-(trifluoromethyl)phenyl]amino}benzonitrile (986 mg, 3.21 mmol) is added to a round-bottomed flask and then flushed with nitrogen. The solid is dissolved in methanol (20 mL) and THF (80 mL) and then the solution is cooled to 0° C. $NiCl_2$ (416 mg, 3.21 mmol) and $Boc_2O$ (1.05 g, 4.82 mmol) are added, followed by $NaBH_4$ (1.21 g, 32.1 mmol), which is slowly added with vigorous effervescence. The solution is warmed to room temperature and after 2 hr, the reaction mixture is concentrated and then saturated $NaHCO_3$ (50 mL) and EtOAc (50 mL) are added. The organic phase is separated, dried ($Na_2SO_4$), and purified (gradient 1% EtOAc/Hexane–20% EtOAc/Hexane) to afford tert-butyl 4-{[2-amino-4-(trifluoromethyl)phenyl]amino}benzylcarbamate as a tan oil. The yield is 821 mg (67%).

Tert-butyl 4-{[2-amino-4-(trifluoromethyl)phenyl]amino}benzylcarbamate (216 mg, 0.56 mmol), and 4,5-dichlorophthalic anhydride (110 mg, 0.51 mmol) are added to a 7 ml vial. After diluting with chloroform (4 mL), the reaction vial is placed on an orbit shaker at 40° C. After 18 hr, the reaction mixture is concentrated. Recrystallization gives 2-({[2-[(4-{[(tert-butoxycarbonyl)amino]methyl}phenyl)amino]-5-(trifluoromethyl)phenyl]amino}carbonyl)-4,5-dichlorobenzoic acid, which is dissolved in ethyl acetate (10 mL). After cooling to 0° C., ethyl acetate saturated with HCl (10 mL) is added. After 2 hr the reaction mixture is concentrated and purified by recrystallization to give 2-({[2-{[4-(aminomethyl)phenyl]amino}-5-(trifluoromethyl)phenyl]amino}carbonyl)-4,5-dichlorobenzoic acid hydrochloride. The yield is 92 mg (34%). 1H NMR (400 MHz, DMSO-d6) 13.91 (s, 1H), 10.24 (s, 1H), 8.25 (s, 3H), 8.09 (s, 1H), 8.02 (s, 1H), 7.95, (s, 1H), 7.83 (m, 1H), 7.49 (m, 1 H), 7.43 (d, 2H), 7.36 (m, 1H), 7.21 (d, 2H), 3.97 (m, 2H); HRMS for $C_{22}H_{16}Cl_2F_3N_3O_3$ 498.0584 (M+H)+.

Example 2 According to Method 2

2,3,4,5-tetrabromo-6-({[2-[(4-cyanophenyl)amino]-5-(trifluoromethyl)phenyl]amino}carbonyl)benzenesulfonic acid [viii.]

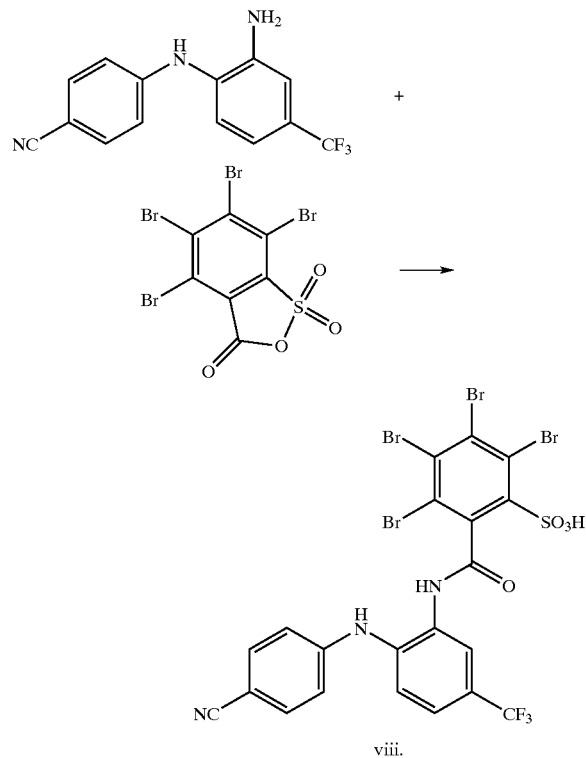

Into a mL are placed -{[2-amino-4-(trifluoromethyl)phenyl]amino}benzonitrile (100 mg, 0.361 mmol), $Et_3N$ (0.15 mL, 1.08 mmol), tetrabromo-2-sulfobenzoic acid cyclic anhydride (270 mg, 0.541 mmol), and THF (5 mL). The mixture is heated with efficient shaking at 40° C. for 16 h. The solution is cooled and 1M HCl is added and the organic phase is extracted with EtOAc (3×). The organic fractions are combined, washed with brine, and concentrated. The crude product is dissolved in MeOH (20 mL) and then Dowex (10 eq) is added. The mixture is efficiently shaken at rt for 16 h. The resin is then filtered and the solution concentrated. The yield is 108 mg of 2,3,4,5-tetrabromo-6-({[2-[(4-cyanophenyl)amino]-5-(trifluoromethyl)phenyl]amino}carbonyl)benzenesulfonic acid, 46%. 1H NMR (400 MHz, DMSO-d6): □ 10.06 (s, 1 H), 8.89 (s, 1 H), 7.70–7.68 (m, 2 H), 7.65–7.61 (m, 2 H), 7.56–7.54 (m, 1 H), 7.32–7.30 (m, 2 H). ESI+ for $C_{21}H_{10}Br_4F_3N_3O_4S$ m/z 778 (M+H)+.

Example 3 According to Method 3

2-({[2-({4-[(benzylamino)methyl]phenyl}amino)-5-(trifluoromethyl)phenyl]amino}carbonyl)-4,5-dichlorobenzoic acid [

In a small round bottom flask equipped with a stirbar, 2-({[2-{[4-(aminomethyl)phenyl]amino}-5-(trifluoromethyl)phenyl]amino}carbonyl)-4,5-dichlorobenzoic acid hydrochloride (0.2 mmol, 107 mg) is combined with benzaldehyde (0.96 mmol, 102 mg) and diluted with 1 mL acetic acid and 4 mL methanol. After 15 minutes, sodium cyanoborohydride (3.5 mmol, 0.24 mL) is added portionwise. After 20 hours, the reaction is stopped. The reaction mixture is made basic with 5N NaOH and extracted three times with ethyl acetate. The organics are combined and washed with brine then dried over $MgSO_4$. After concentration the crude oil is purified by column chromatography (100% EtOAc) to give a white solid in low yield. 1H NMR (400 MHz, DMSO-d6): □ 10.39 (s, 1H), 7.98 (m, 1H), 7.80 (s, 1H), 7.66 (s, 1H), 7.43, (m, 14H), 4.12 (m, 4H). ESI+ for $C_{29}H_{22}Cl_2F_3N_3O_3$ m/z 588 M+.

Example 4 According to Method 4

4,5-dichloro-2-({[2-[(4-{[(morpholin-4-ylcarbonyl)amino]methyl}phenyl)amino]-5-(trifluoromethyl)phenyl]amino}carbonyl)benzoic acid [xix.]

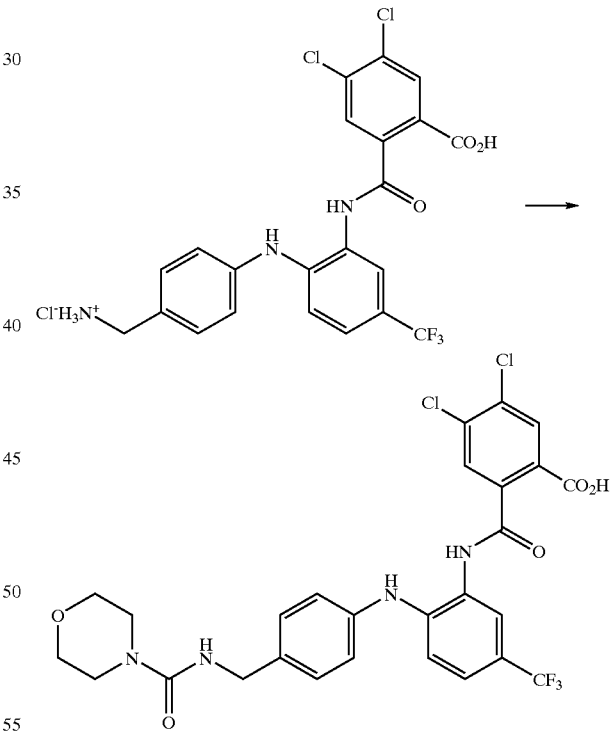

Into a vial are placed 2-({[2-{[4-(aminomethyl)phenyl]amino}-5-(trifluoromethyl)phenyl]amino}carbonyl)-4,5-dichlorobenzoic acid hydrochloride (100 mg, 0.187 mmol), 4-morpholine-carbonylchloride (28 mg, 0.187 mmol), $Et_3N$ (0.08 mL, 0.573 mmol), and THF (10 mL). The mixture is heated with efficient stirring at 40° C. for 4 h. The solution is concentrated and purified by preparative thin layer chromatography. The yield is 31 mg of 4,5-dichloro-2-({[2-[(4{[(morpholin-4-ylcarbonyl)amino]methyl}phenyl)amino]-5-(trifluoromethyl)phenyl]amino}carbonyl)benzoic acid, 27%. 1H NMR (400 MHz, DMSO-d6): □ 13.88 (s, 1 H), 10.14 (s, 1 H), 8.09 (s, 2 H), 7.77 (s, 1 H), 7.70 (s, 1 H), 7.44–7.42 (m, 1 H), 7.26–7.23 (m, 3 H), 7.14–7.09 (m, 3 H), 4.22–4.21 (m, 2 H), 3.56–3.54 (m, 4 H), 3.30–3.28 (m, 4 H)
7.44–7.42 (m, 1 H), 7.26–7.23 (m, 3 H), 7.14–7.09 (m, 3 H),
4.22–4.21 (m, 2 H), 3.56–3.54 (m, 4 H), 3.30–3.28 (m, 4 H).
HRMS for $C_{27}H_{23}Cl_2F_3N_4O_5$ m/z 611.1071 M+.

Example 5 According to Method 5

2-({[2-[(4-cyanophenyl)amino]-5-(trifluoromethyl)phenyl]amino}sulfonyl)benzoic acid [xxiv.]

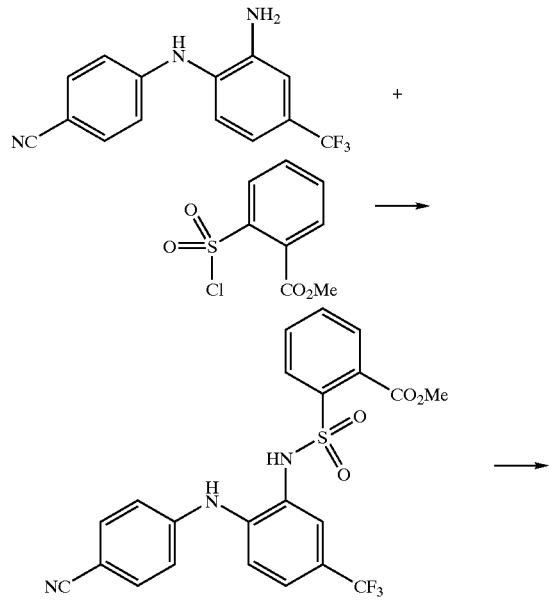

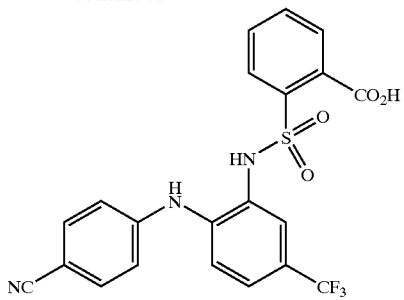

Into a vial are placed 4-{[2-amino-4-(trifluoromethyl)phenyl]amino}benzonitrile (200 mg, 0.721 mmol), methyl 2-(chlorosulfonyl)benzoate (254 mg, 1.08 mmol), and pyridine 10 mL. The mixture is heated with efficient shaking at 40° C. for 16 h. The solution is concentrated and purified by preparative thin layer chromatography. The yield is 289 mg of methyl 2-({[2-[(4-cyanophenyl)amino]-5-(trifluoromethyl)phenyl]amino}sulfonyl)benzoate, 84%).

Into a vial are placed methyl 2-({[2-[(4-cyanophenyl)amino]-5-(trifluoromethyl)phenyl]amino}sulfonyl)benzoate (289 mg, 0.608 mmol), 1M NaOH (10 mL), and MeOH (10 mL). The mixture is efficiently shaken at rt for 16 h. 1M HCl is added to adjust the pH to 1. The precipitated was filtered and purified by preparative thin layer chromatography. The yield is 65 mg of 2-({[2-[(4-cyanophenyl)amino]-5-(trifluoromethyl)phenyl]amino}sulfonyl)benzoic acid, 23%). 1H NMR (400 MHz, DMSO-d6): □ 10.92 (s, 1 H), 9.98 (s, 1 H), 7.58–7.56 (m, 3 H), 7.44–7.43 (m, 2 H), 7.38–7.30 (m, 3 H), 7.21–7.17 (m, 1 H), 7.02–7.00 (m, 2 H). HRMS for $C_{21}H_{14}F_3N_3O_4S$ 462.0754 (M+H)+.

Example 6 According to Method 6

2-({[2-[[4-(aminomethyl)phenyl](methyl)amino]-5-(trifluoromethyl)phenyl]amino}carbonyl)-4,5-dichlorobenzoic acid [xxvii.]

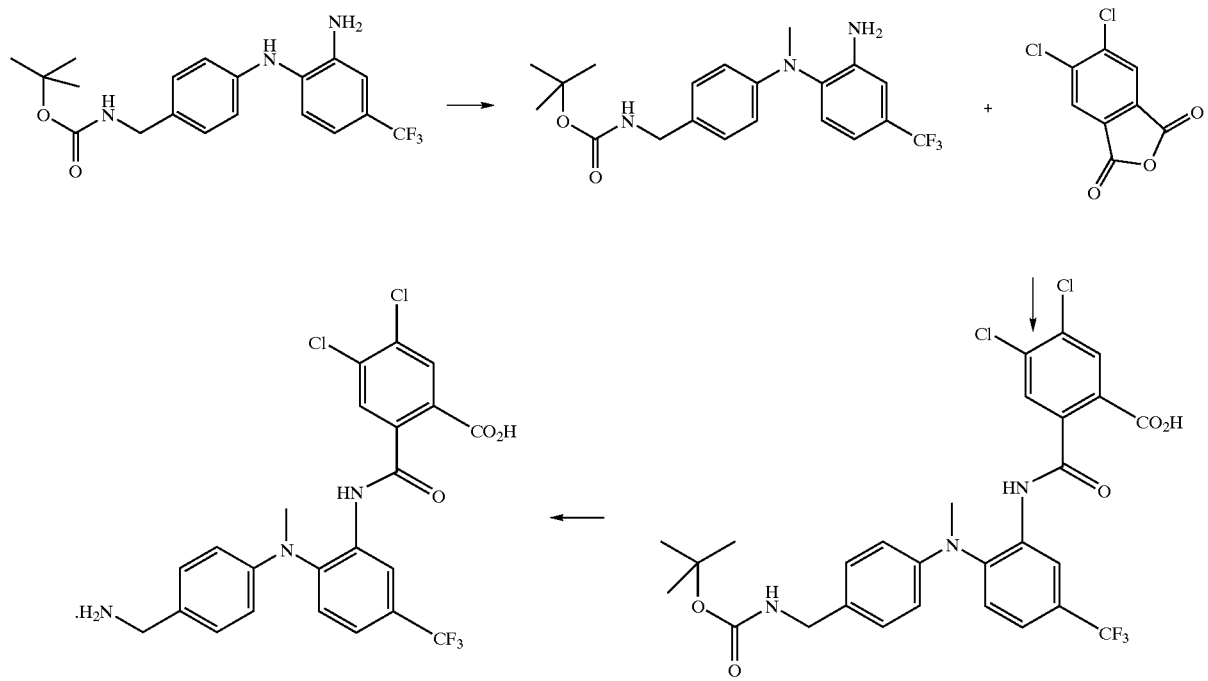

xxvii

Into a round-bottomed flask are placed tert-butyl 4-{[2-amino-4-(trifluoromethyl)phenyl]amino}benzylcarbamate (317 mg, 0.831 mmol), NaH (60% in mineral oil, 37 mg, 0.914 mmol), and DMF (5 mL). The mixture is cooled to 0° C. and efficiently stirred for 1 h. MeI (0.26 mL, 4.16 mmol) is then added and the solution is warmed to rt over 1 h with efficient stirring. $H_2O$ is added and the solution is extracted with $CH_2Cl_2$ (3×) and the combined organic fractions are washed with $H_2O$ (5×). The solution is concentrated and purified by preparative thin layer chromatography. The yield is 179 mg of tert-butyl 4-[[2-amino-4-(trifluoromethyl)phenyl](methyl)amino]benzylcarbamate, 54%.

Into a vial are placed tert-butyl 4-[[2-amino-4-(trifluoromethyl)phenyl](methyl)amino]benzylcarbamate (179 mg, 0.452 mmol), 4,5-dichlorophthalic anhydride (98 mg, 0.452 mmol), and $CHCl_3$. The mixture is heated with efficient shaking at 40° C. for 16 h. The solution is concentrated and the product purified by preparative thin layer chromatography. The yield is 34 mg of 2-({[2-[(4-{[(tert-butoxycarbonyl)amino]methyl}phenyl)(methyl)amino]-5-(trifluoromethyl)phenyl]amino}carbonyl)-4,5-dichlorobenzoic acid, 12%.

Into a vial is placed 2-({[2-[(4-{[(tert-butoxycarbonyl)amino]methyl}phenyl)(methyl)amino]-5-(trifluoromethyl)phenyl]amino}carbonyl)-4,5-dichlorobenzoic acid (34 mg, 0.056 mmol) and MeOH (5 mL) saturated with HCl. The mixture is stirred at rt for 2 h. The solution is concentrated and the product purified by preparative thin layer chromatography. The yield is 12 mg of 2-({[2-[[4-(aminomethyl)phenyl](methyl)amino]-5-(trifluoromethyl)phenyl]amino}carbonyl)-4,5-dichlorobenzoic acid, 42%. DMSO: 13.3 (s, 1 H), 8.48 (s, 1 H), 7.76 (s, 2 H), 7.51 (m, 1 H), 7.41 (m, 1 H), 7.16 (m, 2 H), 6.60–6.58 (m, 2 H), 3.81 (s, 2 H), 3.22 (s, 3 H). ESI+ for $C_{23}H_{18}Cl_2F_3N_3O_3$ 497 (M+H)+.

Example 7

Other Non-Limiting Examples of Compounds of this Invention Include i. 2-[[[2-[[4-(Aminomethyl)phenyl]amino]-5-(trifluoromethyl)phenyl]amino]carbonyl]-4,5-dichlorobenzoic acid monohydrochloride;
ii. 2-({[2-({4-[(benzylamino)methyl]phenyl}amino)-5-(trifluoromethyl)phenyl]amino}carbonyl)-4,5-dichlorobenzoic acid;
iii. N-{5-tert-butyl-2-[(4-cyanophenyl)amino]phenyl}-4,5-dichloro-2-hydroxybenzamide;
iv. (4-{[2-[(2,3,4,5-tetrabromo-6-sulfobenzoyl)amino]-4-(trifluoromethyl)phenyl]amino}phenyl)methanaminium chloride;
v. 4,5-dichloro-2-({[2-[(4-cyanophenyl)amino]-5-(trifluoromethyl)phenyl]amino}carbonyl)benzoic acid;
vi. 3,6-dichloro-2-({[2-[(4-cyanophenyl)amino]-5-(trifluoromethyl)phenyl]amino}carbonyl)benzoic acid;
vii. 2-({[2-[(4-cyanophenyl)amino]-5-(trifluoromethyl)phenyl]amino}carbonyl)-3,4,5,6-tetrafluorobenzoic acid;
viii. 2,3,4,5-tetrabromo-6-({[2-[(4-cyanophenyl)amino]-5-(trifluoromethyl)phenyl]amino}-carbonyl)benzenesulfonic acid;
ix. 2,3,4,5-tetrachloro-6-({[2-[(4-cyanophenyl)amino]-5-(trifluoromethyl)phenyl]amino}-carbonyl)benzoic acid;
x. (4-{[2-[(2-sulfobenzoyl)amino]-4-(trifluoromethyl)phenyl]amino}phenyl)methanaminium chloride;
xi. (4-{[2-({[(1S,2S)-2-carboxycyclohexyl]carbonyl}amino)-4-(trifluoromethyl)phenyl]amino}phenyl)methanaminium chloride;
xii. 2-({[2-[(4-cyanophenyl)amino]-5-(trifluoromethyl)phenyl]amino}-carbonyl)benzenesulfonic acid;
xiii. 2,3,4,5-tetrabromo-6-({[2-[(4-cyanophenyl)amino]-5-(trifluoromethyl)phenyl]amino}-carbonyl)benzoic acid;
xiv. (1R,2R)-2-({[2-[(4-cyanophenyl)amino]-5-(trifluoromethyl)phenyl]amino}carbonyl)-cyclohexanecarboxylic acid
xv. disodium 2-{[2-{[(6-carboxylatocyclohex-3-en-1-yl)carbonyl]amino}-4-(trifluoromethyl)phenyl]amino}benzoate;
xvi. 2-({[2-[(4-cyanophenyl)amino]-5-(trifluoromethyl)phenyl]amino}carbonyl)-3,6-dimethoxybenzoic acid;
xvii. 2-({[2-[(4-cyanophenyl)amino]-5-(trifluoromethyl)phenyl]amino}carbonyl)benzoic acid;
xviii. (1S,2S)-2-({[2-[(4-cyanophenyl)amino]-5-(trifluoromethyl)phenyl]amino}carbonyl)cyclohexanecarboxylic acid;
xix. 4,5-dichloro-2-({[2-[(4-{[(morpholin-4-ylcarbonyl)amino]methyl}phenyl)amino]-5-(trifluoromethyl)phenyl]amino}carbonyl)benzoic acid;
xx. disodium 2-{[2-({[(1S,2R)-2-carboxylate-4,5-dihydroxycyclohexyl]-carbonyl}amino)-4-(trifluoromethyl)phenyl]amino}benzoate;
xxi. (1R,2R)-2-({[2-[(4-cyanophenyl)amino]-5-(trifluoromethyl)phenyl]amino}carbonyl)cyclohexanecarboxylic acid;
xxii. 3-({[2-[(4-cyanophenyl)amino]-5-(trifluoromethyl)phenyl]amino}-carbonyl)-5,6-dihydro-1,4-dithiine-2-carboxylic acid;
xxiii. 3-({[2-[(4-cyanophenyl)amino]-5-(trifluoromethyl)phenyl]amino}carbonyl)isonicotinic acid;
xxiv. 2-({[2-[(4-cyanophenyl)amino]-5-(trifluoromethyl)phenyl]amino}sulfonyl)benzoic acid;
xxv. 2,3,4,5-tetrabromo-6-[({5-tert-butyl-2-[(4-cyanophenyl)amino]phenyl}amino)carbonyl]-benzenesulfonic acid;
xxvi. 2-({[2-[(4-cyanophenyl)amino]-5-(trifluoromethyl)phenyl]amino}carbonyl)cyclopent-1-ene-1-carboxylic acid;
xxvii. 3-({[2-[(4-cyanophenyl)amino]-5-(trifluoromethyl)phenyl]amino}carbonyl)pyrazine-2-carboxylic acid;
xxviii. 2-({[2-[[4-(aminomethyl)phenyl](methyl)amino]-5-(trifluoromethyl)phenyl]amino}-carbonyl)-4,5-dichlorobenzoic acid;
xxix. (1R,2S)-2-({[2-[(4-cyanophenyl)amino]-5-(trifluoromethyl)phenyl]amino}-carbonyl)cyclohexanecarboxylic acid and
xxx. 4-tert-butyl-2-({[2-[(4-cyanophenyl)amino]-5-(trifluoromethyl)phenyl]amino}-carbonyl)benzoic acid.

Spectral data for the compounds are given in the following table:

| Compound No. | Method Scheme | 1H NMR | LRMS | HRMS | Ion |
|---|---|---|---|---|---|
| xiv. | 1 | DMSO: 12.21(s, 1H), 9.65(s, 1H), 8.25(s, 1H), 7.97(s, 1H), 7.65–7.61 (m 2H), 7.52–7.46(m, 2H), 7.01–6.99(m, 2H), 2.63–2.51(m, 2H), 2.05–1.98(m, 1H), 1.88–1.81 (m, 1H), 1.76–1.69(m, 2H), 1.32–1.17(m, 4H) | | 432.1546 | (M + H)+ |
| xxix. | 1 | DMSO: 12.14(s, 1H), 9.41(s, 1H), 8.31(s, 1H), 7.90(s, 1H), 7.63–7.61 (m, 2H), 7.51–7.46(m, 2H), 6.99–6.97(m, 2H), 2.90–2.86 (m, 1H), 2.73–2.68(m, 1H), 2.11–2.03 (m, 1H), 1.79–1.51(m, 4H), 1.44–1.26(m, 3H) | | 432.1519 | (M + H)+ |
| xi. | 1 | DMSO: 12.23(s, 1H), 9.86(s, 1H), 7.93(s, 1H), 7.79(s, 1H) 7.41–7.39 (m, 3H), 7.34–7.32(m, 1H), 7.17–7.15(m, 2H), 3.98–3.94 (m, 2H), 2.70–2.62(m, 1H), 2.59–2.51 (m, 1H), 2.08–1.99(m, 2H), 1.79–1.70(m, 2H), 1.37–1.21 (m, 4H) | | 437.192 | (M + H)+ |
| xviii. | 1 | DMSO: 12.21(s, 1H), 9.65(s, 1H), 8.25(s, 1H), 7.97(s, 1H), 7.65–7.61 (m 2H), 7.52–7.46(m, 2H), 7.01–6.99(m, 2H), 2.63–2.51(m, 2H), 2.05–1.98(m, 1H), 1.88–1.81 (m, 1H), 1.76–1.69(m, 2H), 1.32–1.17(m, 4H) | | 432.1546 | (M + H)+ |
| xxi. | 1 | DMSO: 12.21(s, 1H), 9.65(s, 1H), 8.25(s, 1H), 7.97(s, 1H), 7.65–7.61 (m 2H), 7.52–7.46(m, 2H), 7.01–6.99(m, 2H), 2.63–2.51(m, 2H), 2.05–1.98(m, 1H), 1.88–1.81 (m, 1H), 1.76–1.69(m, 2H), 1.32–1.17(m, 4H) | | 432.1546 | (M + H)+ |
| xiii. | 1 | DMSO: 10.55(s, 1H), 7.96(s, 1H), 7.90(s, 1H), 7.70–7.68(m, 2H), 7.63–7.58(m, 2H), 7.14–7.11 (m, 2H) | 740 | | (M − H)− |
| xxvi. | 1 | DMSO: 13.14(s, 1H), 10.21(s, 1H), 8.44(s, 1H), 7.91(s, 1H), 7.67–7.65 (m, 2H), 7.56–7.51(m, 2H), 7.11–7.09(m, 2H), 2.74–2.64 (m, 4H), 1.93–1.85(m, 2H) | | 416.1233 | (M + H)+ |
| xxii. | 1 | DMSO: 8.88(s, 1H), 7.82–7.81 (m, 1H), 7.71–7.67(m, 3H), 7.58–7.56 (m, 1H), 7.19–7.16(m, 2H), 3.43(s, 4H) | 464 | | (M − H)− |
| xvii. | 1 | (DMSO) 13.39(s, 1H), 10.15(s, 1H), 8.44(s, 1H), 7.96(s, 1H), 7.91 (d, 1H), 7.66,(m, 3H), 7.56(m, 3H), 7.13(m, 2H) | 424 | | (M − H)− |
| i. | 1 | (DMSO) 13.91(s, 1H), 10.24(s, 1H), 8.25(s, 3H), 8.09(s, 1H), 8.02 (s, 1H), 7.95,(s, 1H), 7.83(m, 1H), 7.49(m, 1H), 7.43(d, 2H), 7.36 (m, 1H), 7.21(d, 2H), 3.97(m, 2H) | | 498.0584 | (M + H)+ |
| ix. | 1 | (DMSO) 10.59(s, 1H), 8.09(s, 1H), 8.00(s, 1H), 7.66(m, 2H), 7.60(s, 2H), 7.05(m, 2H) | 564 | | (M + H)+ |
| vii. | 1 | (DMSO) 10.52(s, 1H), 8.32(s, 1H), 8.01(s, 1H), 7.65(m, 2H), 7.57(m, 2H), 7.04(m, 1H) | 498 | 498.0691 | (M + H)+ |
| v. | 1 | (DMSO) 13.80(s, 1H), 10.21(s 1H), 8.50(s, 1H), 8.06(s, 1H), 7.96 (s, 1H), 7.76(s, 1H), 7.67(m, 2H), 7.56(s, 2H), 7.10(m, 2H) | 492 | | (M − 1)− |
| vi. | 1 | (DMSO) 10.53(s, 1H), 8.01(s, 1H), 7.95(s, 1H), 7.68(m, 4H), 7.60(m, 2H), 7.08(m, 2H) | 492 | | (M − 1)− |
| xxiii. | 1 | (DMSO) 10.39–10.27(m, 1H), 9.13–8.75(m, 2H), 8.56–8.41(m, 1H), 8.03–7.96(m, 1H), 7.81–7.50 (m, 5H), 7.16–7.03(M, 2H) | 427 | 427.1014 | (M + H)+ |

-continued

| Compound No. | Method Scheme | 1H NMR | LRMS | HRMS | Ion |
|---|---|---|---|---|---|
| xvi. | 1 | (DMSO) 8.13(s, 1H), 7.59(m, 3H), 7.53(m, 1H), 7.22(m, 2H), 7.14 (m, 2H), 3.87(s, 3H), 3.81(s, 3H) | 486 | 486.13 | (M + H)+ |
| xxvii. | 1 | (DMSO) 13.90(s, 1H), 10.39(s, 1H), 8.93(m, 1H), 8.86(m, 1H), 8.67(s, 1H), 8.23(s, 1H), 7.63(m, 2H), 7.58(s, 2H), 7.05(m, 2H) | 428 | 428.0983 | (M + H)+ |
| ii. | 1 | (DMSO) 10.03(s, 1H), 8.10(s, 0.5H), 8.02(s, 1H), 7.63(s, 0.5H), 7.55(m, 3H), 7.29(m, 2H), 6.89 (m, 2H), 1.31(s, 9H) | 483 | | (M + H)+ |
| xxx. | 1 | (DMSO) 11.17–11.02(m, 1H), 9.99–9.84(m, 1H), 7.93–7.29(m, 10H), 1.37–1.20,(m, 9H) | 482 | 482.1703 | (M + H)+ |
| xii. | 2 | DMSO: 10.26(s, 1H), 9.16(s, 1H), 7.91–7.87(m, 2H), 7.69–7.65 (m, 3H), 7.62–7.60(m, 1H), 7.54–7.49 (m, 3H), 7.31–7.29(m, 2H) | | 462.0742 | (M + H)+ |
| viii. | 2 | DMSO: 10.06(s, 1H), 8.89(s, 1H), 7.70–7.68(m, 2H), 7.65–7.61 (m, 2H), 7.56–7.54(m, 1H), 7.32–7.30 (m, 2H) | 778 | | (M + H)+ |
| iv. | 2 | DMSO: 9.95(s, 1H), 8.58(s, 1H), 7.49–7.46(m, 2H), 7.43–7.40(m, 3H), 7.29–7.27(m, 2H), 3.95(s, 2H) | 780 | | (M − H)− |
| x. | 2 | DMSO: 10.24(s, 1H), 8.77(m, 1H), 7.89–7.87(m, 1H), 7.72–7.70 (m, 2H), 7.53–7.51(m, 2H), 7.44–7.37 (m, 4H), 7.26–7.24(m, 2H), 3.90–3.86(m, 2H) | | 449.0799 | (M − NH2)− |
| xxv. | 2 | DMSO: 9.74(s, 1H), 8.51(s, 1H), 7.57–7.55(m, 2H), 7.40–7.38(m, 2H), 7.28–7.26(m, 1H), 7.15–7.13 (m, 2H), 1.30(s, 9H) | 766 | | (M + H)+ |
| ii. | 3 | (DMSO) 10.39(s, 1H), 7.98(m, 1H), 7.80(s, 1H), 7.66(s, 1H), 7.43,(m, 14H), 4.12(m, 4H) | 588 | | M+ |
| xix. | 4 | DMSO: 13.88(s, 1H), 10.14(s, 1H), 8.09(s, 2H), 7.77(s, 1H), 7.70 (s, 1H), 7.44–7.42(m, 1H), 7.26–7.23 (m, 3H), 7.14–7.09(m, 3H), 4.22–4.21(m, 2H), 3.56–3.54(m, 4H), 3.30–3.28(m, 4H) | | 611.1071 | M+ |
| xxiv. | 5 | DMSO: 10.92(s, 1H), 9.98(s, 1H), 7.58–7.56(m, 3H), 7.44–7.43 (m, 2H), 7.38–7.30(m, 3H), 7.21–7.17 (m, 1H), 7.02–7.00(m, 2H) | | 462.0754 | (M + H)+ |
| xxvii. | 6 | DMSO: 13.3(s, 1H), 8.48(s, 1H), 7.76(s, 2H), 7.51(m, 1H), 7.41 (m, 1H), 7.16(m, 2H), 6.60–6.58 (m, 2H), 3.81(s, 2H), 3.22(s, 3H) | 497 | | (M + H)+ |

Example 8

Evaluation of Polymerase Activity

Compounds of the present invention are evaluated for inhibition of HCV NS5b RNA dependent RNA polymerase activity in assays comprised of a suitable buffer (e.g. 20 mM Tris-HCl pH 7.6), primed or unprimed RNA templates, GTP, ATP, CTP, and UTP, $MnCl_2$ or $MgCl_2$, and reducing agent such as 10 mM dithiothreitol or 2-mercaptoethanol. The assay buffer may contain salts such as ammonium acetate, KCl, or NaCl, and nonionic or zwitterionic detergents such as Tween or CHAPS. The incorporation of nucleotides into the complementary RNA strand may be monitored by the incorporation of radiolabeled NTP (e.g. $^3H$ labeled GTP). Suitable RNA templates for de novo initiation in the presence of 20–50 μM GTP or ATP are the homopolymers poly rC and poly rU, respectively. Heteropolymer RNA templates with 1–3 cytidine (C) bases or 1–3 uridine (U) bases at the 3' terminus of the template may also be used for de novo initiation. Primed RNA templates such as poly rC primed with oligo rG or oligo dG, and poly rA primed with oligo rU may also be used to detect polymerase activity. The primers may be any length greater than 10 bases. A biotin residue may be added to the 5' end of the template or the 5' end of the primer to capture the template and the newly synthesized, complementary strand on avidin coated spheres. One embodiment of this technology consists of a mixture of NS5b polymerase, a poly rC RNA template primed with 5' biotinylated oligo rG, 20 mM Tris HCl pH 7.6, 100 mM ammonium acetate, 10 mM dithiothreitol, 2 mM CHAPS, 1 mM $MgCl_2$, and 150–200 nM $^3H$ labeled GTP. Test compounds (inhibitors) may be incorporated in the reaction mixture with up to 10% DMSO. The reaction is run for various times (1–180 minutes) at 22–37° C., and stopped by the addition of 10–140 mM EDTA. Scintillation Proximity Assay avidin-coated beads (Amersham Pharmacia Biotech) are added to capture the ds RNA product; or the reaction mixtures may be transferred to avidin coated Flash Plates (Perkin Elmer Life Sciences). The incorporation of radiolabeled GTP into the complementary strand is measured in 96, 384, or 1536 well plates in scintillation counters such as the Wallac Microbeta and Packard TopCount.

Biological data for selected compounds using this assay are presented in Table 2 and given as the concentration in micromolar required for 50% inhibition.

TABLE 2

| i. | 1.42 |
|---|---|
| xvii. | 1.74 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a viral infection comprising administering to an animal in need thereof an effective amount of a compound of Formula I:

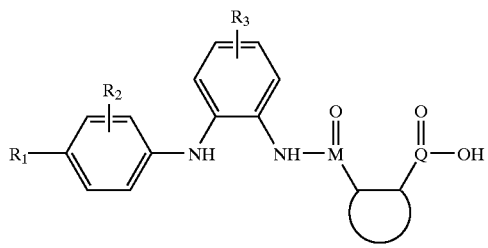

Formula I wherein

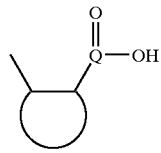

represents a substituted or unsubstituted five or six membered saturated, partially unsaturated or aromatic ring optionally containing 1 or 2 heteroatoms of O, N or S;

$R_2$ and $R_3$ represent 1 to three substituents independently selected from the group consisting of halogen, —CN, N(R)(R'), —NO$_2$, fluoro-C$_1$–C$_8$-alkyl, fluoro-C$_1$–C$_8$-alkyloxy, C$_1$–C$_8$-alkyl, aryl, ara-C$_1$–C$_8$-alkyl, arlyoxy, ara-C$_1$–C$_8$-alkyloxy, —C$_1$–C$_8$-alkylthio, arylthio, and hetero-C$_1$–C$_8$-alkyl;

R, R' and R" are independently H or C$_1$–C$_8$ alkyl;

R and R' may be taken together to form a 3 to 7 membered ring optionally containing an additional heteroatom of —O—, —NR"—, —S— or —SO$_n$—;

$R_1$ is selected from the group consisting of H, —CN, and —(CH$_2$)$_n$—N(R$_5$)R$_6$;

$R_5$ is H or C$_1$–C$_8$ alkyl;

$R_6$ is selected from the group consisting of H, C$_1$–C$_8$ alkyl, aryl, substituted aryl, ara-C$_1$–C$_8$-alkyl, heteroaryl, heteroara-C$_1$–C$_8$-alkyl, hetero-C$_1$–C$_8$-alkyl and substituted hetero-C$_1$–C$_8$-alkyl;

$R_5$ and $R_6$ may be joined together to form a 5 to 7 membered ring optionally containing an additional heteroatom of —NR—, —O—, —S— or —SO$_n$—;

M and Q are independently —C— or —S(=O)—;

Each n is independently 0, 1 or 2.

2. The method of claim 1, wherein said viral infection is hepatitis infection.

3. The method of claim 1, wherein said viral infection is hepatitis C virus infection.

4. The method of claim 1, wherein:

$R_1$ is —(CH$_2$)$_n$—N(R$_5$)R$_6$;

$R_5$ is H or C$_1$–C$_8$ alkyl;

$R_6$ is selected from the group consisting of H, C$_1$–C$_8$ alkyl, —C(=NH)NH$_2$, aryl, substituted aryl, ara-C$_1$–C$_8$-alkyl, heteroaryl, heteroara-C$_1$–C$_8$-alkyl, hetero-C$_1$–C$_8$-alkyl and substituted hetero-C$_1$–C$_8$-alkyl;

$R_5$ and $R_6$ may be joined together to form a 5 to 7 membered ring optionally containing an additional heteroatom of —NR—, —O—, —S— or —SO$_n$—;

Each n is independently 0, 1 or 2.

5. A method for treating a viral infection comprising administering, to an animal in need thereof, an effective amount of 1–3 compounds of Formula 1 in combination with other antiviral agents which are either therapeutic or prophylactic agents.

6. The method of claim 5, wherein the other antiviral agents are interferon alfa-2b, interferon alfa-2a, interferon alfacon-1 and ribavarin.

7. The method of claim 5, wherein the other antiviral agent is interferon alfa-2b, interferon alfa-2a, or interferon alfacon-1.

8. The method of claim 5, wherein the other antiviral agent is ribavarin.

9. A compound of Formula 1

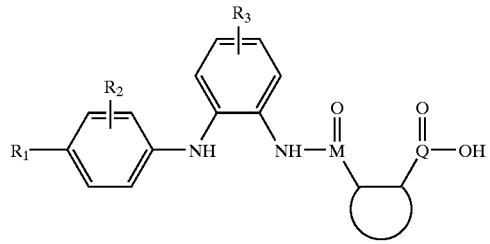

Formula I wherein

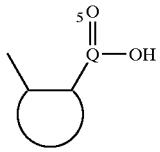

represents a substituted or unsubstituted five or six membered saturated, partially unsaturated or aromatic ring optionally containing 1 or 2 heteroatoms of O, N or S;

$R_2$ and $R_3$ represent 1 to three substituents independently selected from the group consisting of halogen, —CN, N(R)(R'), —NO$_2$, fluoro-$C_1$–$C_8$-alkyl, fluoro-$C_1$–$C_8$-alkyloxy, —$C_1$–$C_8$-alkyl, aryl, ara-$C_1$–$C_8$-alkyl, arlyoxy, ara-$C_1$–$C_8$-alkyloxy, —$C_1$–$C_8$-alkylthio, arylthio, and hetero-$C_1$–$C_8$-alkyl;

R, R' and R" are independently H or $C_1$–$C_8$ alkyl;

R and R' may be taken together to form a 3 to 7 membered ring optionally containing an additional heteroatom of —O—, —NR"—, —S— or —SO$_n$—;

$R_1$ is selected from the group consisting of H, —CN, and —(CH$_2$)$_n$—N(R$_5$)R$_6$;

$R_5$ is H or $C_1$–$C_8$ alkyl;

$R_6$ is selected from the group consisting of H, $C_1$–$C_8$ alkyl, aryl, substituted aryl, ara-$C_1$–$C_8$-alkyl, heteroaryl, heteroara-$C_1$–$C_8$-alkyl, hetero-$C_1$–$C_8$-alkyl and substituted hetero-$C_1$–$C_8$-alkyl;

$R_5$ and $R_6$ may be joined together to form a 5 to 7 membered ring optionally containing an additional heteroatom of —NR—, —O—, —S— or —SO$_n$—;

M and Q are independently —C— or —S(=O)—;

Each n is independently 0, 1 or 2.

10. A compound of claim 9, wherein:

$R_1$ is —(CH$_2$)$_n$—N(R$_5$)R$_6$;

$R_5$ is H or $C_1$–$C_8$ alkyl;

$R_6$ is selected from the group consisting of H, $C_1$–$C_8$ alkyl, aryl, substituted aryl, aralkyl, heteroaryl, hetero-$C_1$–$C_8$-aralkyl, hetero-$C_1$–$C_8$-alkyl, and substituted hetero-$C_1$–$C_8$-alkyl;

$R_5$ and $R_6$ may be joined together to form a 5 to 7 membered ring optionally containing an additional heteroatom of —NR—, —O—, —S— or —SO$_n$—;

Each n is independently 0, 1 or 2.

11. A compound according to claim 10 selected from the group comprised of:

2-[[[2-[[4-(aminomethyl)phenyl]amino]-5-(trifluoromethyl)phenyl]amino]carbonyl]-4,5-dichlorobenzoic acid monohydrochloride;

2-({[2-({4-[(benzylamino)methyl]phenyl}amino)-5-(trifluoromethyl)phenyl]amino}carbonyl)-4,5-dichlorobenzoic acid;

N-{5-tert-butyl-2-[(4-cyanophenyl)amino]phenyl}-4,5-dichloro-2-hydroxybenzamide;

(4-{[2-[(2,3,4,5-tetrabromo-6-sulfobenzoyl)amino]-4-(trifluoromethyl)phenyl]amino}phenyl)methanaminium chloride;

4,5-dichloro-2-({[2-[(4-cyanophenyl)amino]-5-(trifluoromethyl)phenyl]amino}carbonyl)benzoic acid;

3,6-dichloro-2-({[2-[(4-cyanophenyl)amino]-5-(trifluoromethyl)phenyl]amino}carbonyl)benzoic acid;

2-({[2-[(4-cyanophenyl)amino]-5-(trifluoromethyl)phenyl]amino}carbonyl)-3,4,5,6-tetrafluorobenzoic acid;

2,3,4,5-tetrabromo-6-({[2-[(4-cyanophenyl)amino]-5-(trifluoromethyl)phenyl]amino}-carbonyl)benzenesulfonic acid;

2,3,4,5-tetrachloro-6-({[2-[(4-cyanophenyl)amino]-5-(trifluoromethyl)phenyl]amino}-carbonyl)benzoic acid;

(4-{[2-[(2-sulfobenzoyl)amino]-4-(trifluoromethyl)phenyl]amino}phenyl)methanaminium chloride;

(4-{[2-({[(1S,2S)-2-carboxycyclohexyl]carbonyl}amino)-4-(trifluoromethyl)phenyl]amino}phenyl)methanaminium chloride;

2-({[2-[(4-cyanophenyl)amino]-5-(trifluoromethyl)phenyl]amino}-carbonyl)benzenesulfonic acid;

2,3,4,5-tetrabromo-6-({[2-[(4-cyanophenyl)amino]-5-(trifluoromethyl)phenyl]amino}-carbonyl)benzoic acid;

(1R,2R)-2-({[2-[(4-cyanophenyl)amino]-5-(trifluoromethyl)phenyl]amino}carbonyl)-cyclohexanecarboxylic acid disodium 2-{[2-{[(6-carboxylatocyclohex-3-en-1-yl)carbonyl]amino}-4-(trifluoromethyl)phenyl]amino}benzoate;

2-({[2-[(4-cyanophenyl)amino]-5-(trifluoromethyl)phenyl]amino}carbonyl)-3,6-dimethoxybenzoic acid;

2-({[2-[(4-cyanophenyl)amino]-5-(trifluoromethyl)phenyl]amino}carbonyl)benzoic acid;

(1S,2S)-2-({[2-[(4-cyanophenyl)amino]-5-(trifluoromethyl)phenyl]amino}carbonyl)cyclohexanecarboxylic acid;

4,5-dichloro-2-({[2-[(4-{[(morpholin-4-ylcarbonyl)amino]methyl}phenyl)amino]-5-(trifluoromethyl)phenyl]amino}carbonyl)benzoic acid;

disodium 2-{[2-({[(1S,2R)-2-carboxylato-4,5-dihydroxycyclohexyl]-carbonyl}amino)-4-(trifluoromethyl)phenyl]amino}benzoate;

(1R,2R)-2-({[2-[(4-cyanophenyl)amino]-5-(trifluoromethyl)phenyl]amino}carbonyl)cyclohexanecarboxylic acid;

3-({[2-[(4-cyanophenyl)amino]-5-(trifluoromethyl)phenyl]amino}-carbonyl)-5,6-dihydro-1,4-dithiine-2-carboxylic acid;

3-({[2-[(4-cyanophenyl)amino]-5-(trifluoromethyl)phenyl]amino}carbonyl)isonicotinic acid;

2-({[2-[(4-cyanophenyl)amino]-5-(trifluoromethyl)phenyl]amino}sulfonyl)benzoic acid;

2,3,4,5-tetrabromo-6-[({5-tert-butyl-2-[(4-cyanophenyl)amino]phenyl}amino)carbonyl]-benzenesulfonic acid;

2-({[2-[(4-cyanophenyl)amino]-5-(trifluoromethyl)phenyl]amino}carbonyl)cyclopent-1-ene-1-carboxylic acid;

3-({[2-[(4-cyanophenyl)amino]-5-(trifluoromethyl)phenyl]amino}carbonyl)pyrazine-2-carboxylic acid;

2-({[2-[[4-(aminomethyl)phenyl](methyl)amino]-5-(trifluoromethyl)phenyl]amino}-carbonyl)-4,5-dichlorobenzoic acid;

(1R,2S)-2-({[2-[(4-cyanophenyl)amino]-5-(trifluoromethyl)phenyl]amino}-carbonyl)cyclohexanecarboxylic acid and 4-tert-butyl-2-({[2-[(4-cyanophenyl)amino]-5-(trifluoromethyl)phenyl]amino}-carbonyl)benzoic acid.

12. A pharmaceutical composition, comprising a pharmaceutically acceptable carrier and a therapeutically or prophylactically effective amount of a compound of any one of claims 9–11.

* * * * *